US012611672B2

(12) United States Patent
Uehara et al.

(10) Patent No.: US 12,611,672 B2
(45) Date of Patent: Apr. 28, 2026

(54) METHOD FOR INTRODUCING LIQUID INTO FLOW PATH DEVICE

(71) Applicant: KYOCERA CORPORATION, Kyoto (JP)

(72) Inventors: Masami Uehara, Higashiomi (JP); Masamitsu Sasahara, Omihachiman (JP)

(73) Assignee: KYOCERA CORPORATION, Kyoto (JP)

( * ) Notice: Subject to any disclaimer, the term of this patent is extended or adjusted under 35 U.S.C. 154(b) by 45 days.

(21) Appl. No.: 18/850,562

(22) PCT Filed: Mar. 2, 2023

(86) PCT No.: PCT/JP2023/007769
§ 371 (c)(1),
(2) Date: Sep. 25, 2024

(87) PCT Pub. No.: WO2023/189163
PCT Pub. Date: Oct. 5, 2023

(65) Prior Publication Data
US 2025/0222452 A1     Jul. 10, 2025

(30) Foreign Application Priority Data
Mar. 31, 2022     (JP) ................................ 2022-059128

(51) Int. Cl.
*B01L 3/00* (2006.01)
*G01N 1/38* (2006.01)
(Continued)

(52) U.S. Cl.
CPC ... *B01L 3/502761* (2013.01); *B01L 3/502746* (2013.01); *B01L 3/502715* (2013.01);
(Continued)

(58) Field of Classification Search
CPC ......... B01L 3/502761; B01L 3/502746; B01L 3/502715; B01L 2200/0647;
(Continued)

(56) References Cited

U.S. PATENT DOCUMENTS

| 2010/0116661 A1* | 5/2010 | Kaji | ..................... | G01N 27/447 |
| | | | | 204/453 |
| 2012/0028349 A1* | 2/2012 | Giorgini | ............... | G01N 1/4077 |
| | | | | 435/325 |

(Continued)

FOREIGN PATENT DOCUMENTS

| WO | 2020/067024 A1 | 4/2020 |

*Primary Examiner* — Minh Q Le
(74) *Attorney, Agent, or Firm* — HAUPTMAN HAM, LLP

(57) ABSTRACT

A method for introducing a liquid into a flow path device includes preparation, filling, first suction, and introduction. The flow path device includes a flow path portion inside to allow a liquid flow between first and second openings. A switcher includes first to third ports. The preparation includes connecting the flow path device and the switcher to allow a liquid flow between the second opening and the first port. The preparation includes connecting the second port and a liquid storage, connecting the third port and a suction-discharge unit, and connecting the first opening and a feeder. The filling includes filling, with a second liquid fed by the feeder, a flow path from the feeder to the liquid storage. The first suction includes sucking a first liquid using the suction-discharge unit from the liquid storage. The introduction includes introducing the first liquid into the flow path portion using the suction-discharge unit.

6 Claims, 21 Drawing Sheets

(51) Int. Cl.

| | |
|---|---|
| *G01N 1/40* | (2006.01) |
| *G01N 33/49* | (2006.01) |
| *G01N 35/10* | (2006.01) |

(52) U.S. Cl.
CPC . *B01L 2200/027* (2013.01); *B01L 2200/0647* (2013.01); *B01L 2200/0652* (2013.01); *B01L 2300/0654* (2013.01); *B01L 2300/0867* (2013.01); *B01L 2300/087* (2013.01); *B01L 2300/0877* (2013.01); *B01L 2300/0883* (2013.01); *B01L 2400/0487* (2013.01); *B01L 2400/049* (2013.01); *G01N 1/38* (2013.01); *G01N 1/4077* (2013.01); *G01N 33/49* (2013.01); *G01N 33/491* (2013.01); *G01N 33/4915* (2013.01); *G01N 35/1009* (2013.01); *G01N 35/1095* (2013.01)

(58) Field of Classification Search
CPC ....... B01L 2200/027; B01L 2200/0652; B01L 2300/0654; B01L 2300/087; B01L 2300/0877; B01L 2300/0883; B01L 2300/0867; B01L 2400/0487; B01L 2400/049; G01N 33/491; G01N 33/4915; G01N 1/38; G01N 1/4077; G01N 35/1095; G01N 35/1009; G01N 33/49
USPC .......................................................... 137/2
See application file for complete search history.

(56) References Cited

U.S. PATENT DOCUMENTS

| | | | |
|---|---|---|---|
| 2012/0040472 A1* | 2/2012 | Churski | B01F 25/4331 |
| | | | 436/180 |
| 2012/0261356 A1* | 10/2012 | Tsutsui | B01L 3/502761 |
| | | | 210/335 |
| 2013/0209328 A1* | 8/2013 | Dresse | F04B 19/006 |
| | | | 264/279 |
| 2016/0199840 A1* | 7/2016 | Tachibana | B01F 25/4314 |
| | | | 435/6.12 |
| 2017/0003270 A1* | 1/2017 | Béguin | B01L 3/50273 |
| 2017/0080424 A1* | 3/2017 | Di Fabrizio | B01L 3/502707 |
| 2019/0309346 A1* | 10/2019 | Stakenborg | C12Q 1/686 |
| 2020/0330989 A1* | 10/2020 | Masuhara | G01N 15/1404 |
| 2020/0338552 A1* | 10/2020 | Scherr | B01L 3/502776 |
| 2021/0162415 A1* | 6/2021 | Shenderov | B01L 3/567 |
| 2021/0322985 A1* | 10/2021 | Yoneta | B01L 3/502761 |
| 2021/0356378 A1 | 11/2021 | Yoneta | |
| 2021/0387194 A1* | 12/2021 | Goto | B01L 3/502784 |
| 2022/0091148 A1* | 3/2022 | Samsoondar | G01N 33/4925 |
| 2022/0266242 A1* | 8/2022 | Samsoondar | B01L 3/502715 |
| 2022/0390431 A1* | 12/2022 | Kubo | B01D 15/34 |
| 2023/0152191 A1* | 5/2023 | Sasahara | G01N 15/1459 |
| | | | 73/863.23 |
| 2023/0256447 A1* | 8/2023 | Rosen | B01L 3/502784 |
| | | | 422/503 |
| 2025/0035659 A1* | 1/2025 | Sasahara | G01N 35/08 |
| 2025/0121375 A1* | 4/2025 | Cumbie | B01L 3/50273 |
| 2025/0137891 A1* | 5/2025 | Ito | G01N 1/14 |

* cited by examiner

METHOD FOR INTRODUCING LIQUID INTO FLOW PATH DEVICE

CROSS-REFERENCE TO RELATED APPLICATION

The present application is a National Phase of International Application No. PCT/JP2023/007769 filed Mar. 2, 2023, which claims priority to Japanese Patent Application No. 2022-59128 filed on Mar. 31, 2022, the entire disclosure of which is incorporated herein by reference.

FIELD

The present disclosure relates to a method for introducing a liquid into a flow path device.

BACKGROUND

With a known technique, a first liquid as a process target and a second liquid for, for example, diluting or transporting the first liquid are introduced into a flow path device to undergo various processes such as separating and measurement of particles contained in the first liquid (refer to, for example, WO 2020/067024). The first liquid is, for example, blood. The second liquid is, for example, saline. The flow path device is, for example, any of various devices including microflow paths.

The first liquid and the second liquid are fed into the flow paths in the flow path device through, for example, a tube connected to a flow inlet in the flow path device. The flow paths containing air may lower the accuracy of the various processes in the flow path device. Thus, for example, the flow paths in the flow path device and the tube are filled with a liquid to remove air before the first liquid and the second liquid are introduced into the flow path device for the various processes.

SUMMARY

One or more aspects of the present disclosure are directed to a method for introducing a liquid into a flow path device.

In an aspect, a method for introducing a liquid into a flow path device includes preparation, filling, first suction, and introduction. The preparation includes establishing a connection between a flow path device and a switcher to allow a liquid flow between a second opening in the flow path device and a first port in the switcher. The flow path device includes a flow path portion inside the flow path device to allow a liquid flow between a first opening and the second opening in the flow path device. The switcher includes the first port, a second port, and a third port and is selectively settable to one of a first state, a second state, or a third state. The preparation includes establishing a connection between the second port and an internal space of a liquid storage to allow a liquid flow between the second port and the internal space. The liquid storage stores a first liquid. The preparation includes establishing a connection between the third port and a suction-discharge unit to allow a liquid flow between the third port and the suction-discharge unit. The suction-discharge unit sucks and discharges a liquid. The preparation includes establishing a connection between the first opening and a liquid feeder to allow a liquid flow between the first opening and the liquid feeder. The liquid feeder feeds a second liquid different from the first liquid. The first state is a state allowing a liquid flow between the first port and the second port. The second state is a state allowing a liquid flow between the second port and the third port. The third state is a state allowing a liquid flow between the first port and the third port. The filling is performed after the preparation with the switcher being set to the first state. The filling includes feeding the second liquid using the liquid feeder to fill, with the second liquid, a flow path from the liquid feeder through the first opening, the flow path portion, the second opening, the first port, and the second port to the liquid storage. The first suction is performed after the filling with the switcher being set to the second state. The first suction includes sucking the first liquid using the suction-discharge unit from the liquid storage through the second port and the third port into the suction-discharge unit. The introduction is performed after the first suction with the switcher being set to the third state. The introduction includes introducing the first liquid using the suction-discharge unit into the flow path portion through the third port, the first port, and the second opening.

BRIEF DESCRIPTION OF THE DRAWINGS

FIG. 12 is a conceptual diagram of the first flow path device and the components, illustrating their example states in a mixing process.

DETAILED DESCRIPTION

Figure 1:
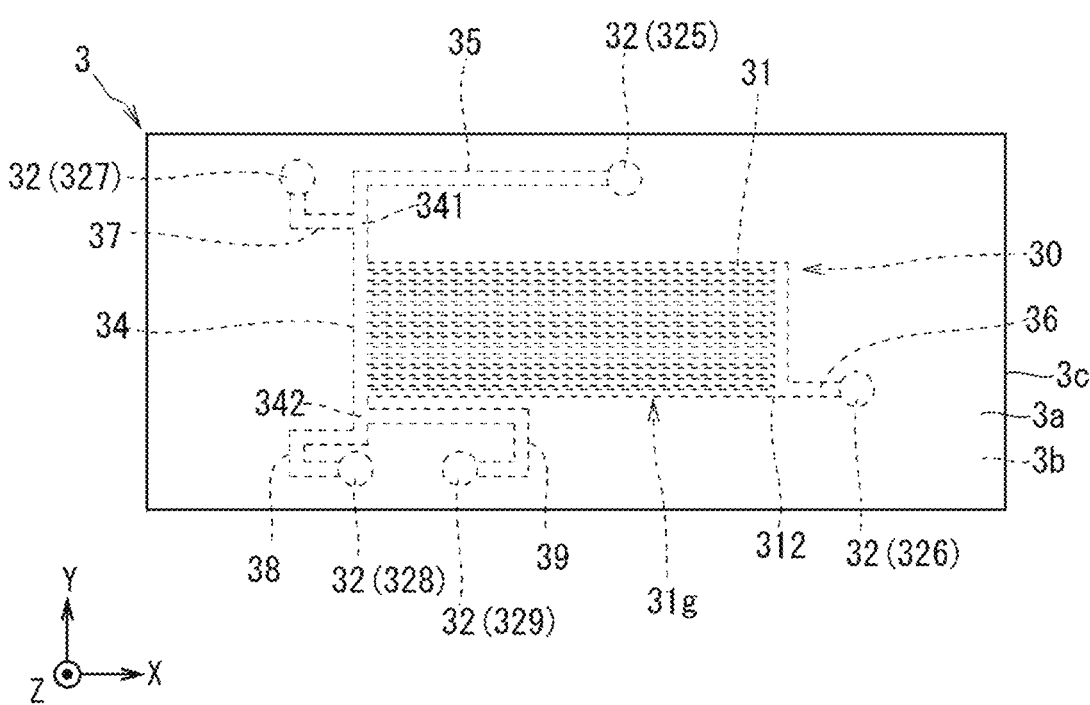
FIG. 1 is a schematic plan view of an example first flow path device according to a first embodiment.

With a known technique, a liquid (also referred to as a first liquid) as a process target and a liquid (also referred to as a second liquid) for, for example, diluting or transporting the first liquid are introduced into a flow path device to undergo various processes such as separating and measurement of particles contained in the first liquid. The first liquid is, for example, blood. The second liquid is, for example, saline. The flow path device is, for example, any of various devices including microflow paths.

The first liquid and the second liquid are fed into the flow paths in the flow path device through, for example, a tube connected to a flow inlet in the flow path device. The flow paths containing air may lower the accuracy of the various processes in the flow path device. Thus, for example, the flow paths in the flow path device and the tube are filled with a liquid to remove air before the first liquid and the second liquid are introduced into the flow path device for the various processes on the first liquid in the flow path device.

For example, the flow path device may include a first flow inlet and a second flow inlet to allow a liquid flow between these ports inside the flow path device, and the first liquid and the second liquid may be respectively introduced into the first flow inlet and the second flow inlet through a preparation process, a first process, a second process, and a third process described below that are performed sequentially.

In the preparation process, using a switching member that switches the liquid flow path between two of its first to third ports, a first feeder that feeds the first liquid is connected to the first port, the second port is connected to a discharge container, the third port is connected to the first flow inlet in the flow path device, and a second feeder that feeds the second liquid is connected to the second flow inlet in the flow path device.

In the first process, the switching member is set to a state allowing a liquid flow between the second port and the third port. In this state, the second liquid is delivered from the second feeder through the second flow inlet, the flow paths in the flow path device, the first flow inlet, and the switching member to the discharge container to fill, with the second liquid, the flow path from the second feeder to the switching member.

In the second process, the switching member is set to a state allowing a liquid flow between the first port and the second port. In this state, the first liquid is delivered from the first feeder through the switching member to the discharge container to fill, with the first liquid, the flow path from the first feeder to the switching member.

In the third process, the switching member is set to a state allowing a liquid flow between the first port and the third port. In this state, the first liquid is delivered from the first feeder through the switching member to be introduced into the first flow inlet, and the second liquid is delivered from the second feeder to be introduced into the second flow inlet.

With the above method, however, the first process may cause a certain amount of the second liquid to be discharged to the discharge container when the second liquid is fed into the flow paths in the flow path device, and the second process may cause a certain amount of the first liquid to be discharged to the discharge container when the first liquid is fed into the flow paths in the flow path device. This may produce a certain amount of waste liquid from wasteful discharge of the first liquid and the second liquid.

Thus, methods for introducing a liquid into a flow path device may be improved to reduce waste liquid.

The inventor of the present disclosure has devised a method for introducing a liquid into a flow path device with less waste liquid.

Embodiments of the present disclosure will now be described with reference to the drawings. In the drawings, the same reference numerals denote the components with the same or similar structures and functions. The components with the same or similar structures and functions will not be described repeatedly. The drawings are schematic.

The drawings may include the right-handed XYZ coordinate system for convenience. A positive Z-direction is hereafter defined as the vertically upward direction (or simply the upward direction). The vertically downward direction is also referred to as a negative Z-direction. The direction opposite to an X-direction is also referred to as a negative X-direction. The direction opposite to a Y-direction is also referred to as a negative Y-direction.

In each of the cross-sectional views in FIGS. 20 to 25, the flow path device is partially cut and not illustrated.

"The flow path" described hereafter has the structure that allows a liquid to flow.

The dimension of the flow path in the direction orthogonal to the direction in which the flow path extends is referred to as the width of the flow path. The flow path having a relatively small width indicates the flow path being relatively narrow. The flow path having a relatively large width indicates the flow path being relatively wide.

1. FIRST EMBODIMENT

1-1. Example Schematic Structure of First Flow Path Device

Figure 2:
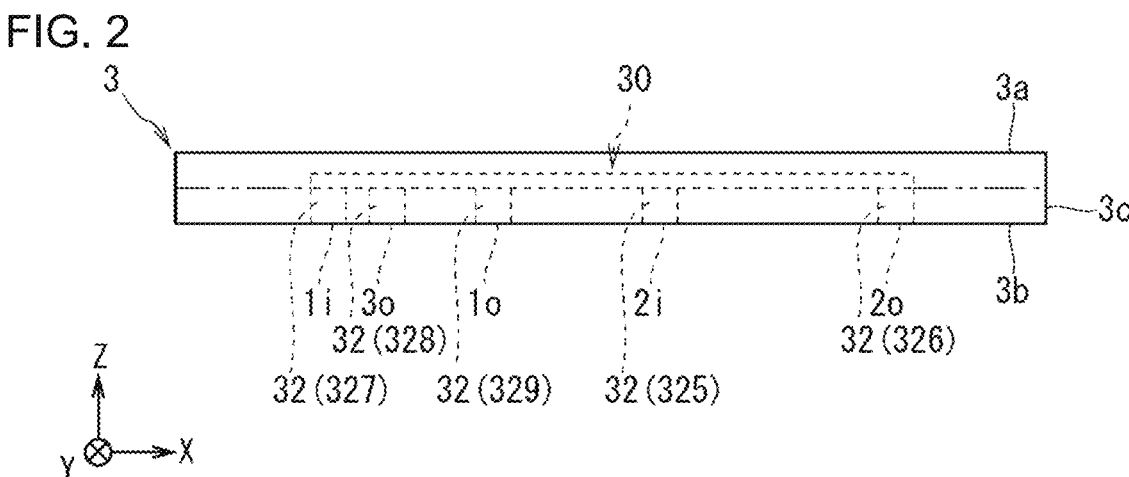
FIG. 2 is a schematic front view of the example first flow path device according to the first embodiment.

FIG. 1 is a schematic plan view of an example flow path device 3 (also referred to as a first flow path device) as a separating flow path device according to a first embodiment. FIG. 2 is a schematic front view of the example first flow path device 3 according to the first embodiment.

In the first embodiment, the first flow path device 3 is, for example, a plate. The first flow path device 3 includes, for example, a surface (also referred to as a first upper surface) 3a, a surface (also referred to as a first lower surface) 3b opposite to the first upper surface 3a, and surfaces (also referred to as first side surfaces) 3c connecting the first upper surface 3a and the first lower surface 3b. In other words, the first flow path device 3 includes an outer surface including the first upper surface 3a, the first lower surface 3b, and the first side surfaces 3c. The first upper surface 3a is located in the positive Z-direction from the first lower surface 3b.

In the examples in FIGS. 1 and 2, the first upper surface 3a faces in the positive Z-direction. In other words, the first upper surface 3a has a normal in the positive Z-direction. The first lower surface 3b faces in the negative Z-direction. In other words, the first lower surface 3b has a normal in the negative Z-direction. The first upper surface 3a and the first lower surface 3b are each, for example, flat and rectangular.

The first flow path device 3 has a thickness of, for example, about 1 to 5 millimeters (mm). The thickness of the first flow path device 3 refers to the dimension of the first flow path device 3 in the positive Z-direction. The first upper surface 3a and the first lower surface 3b of the first flow path device 3 each have a width of, for example, about 10 to 50 mm. The width of the first upper surface 3a refers to the dimension of the first upper surface 3a in a positive X-direction. The width of the first lower surface 3b refers to the dimension of the first lower surface 3b in the positive X-direction. The first upper surface 3a and the first lower surface 3b of the first flow path device 3 each have a length of, for example, about 10 to 30 mm. The length of the first upper surface 3a refers to the dimension of the first upper surface 3a in a positive Y-direction. The length of the first lower surface 3b refers to the dimension of the first lower surface 3b in the positive Y-direction.

The first flow path device 3 includes a flow path portion 30 that is not open in the outer surface of the first flow path device 3, and multiple holes 32 that are each continuous with the flow path portion 30 and are open in the outer surface of the first flow path device 3. "A first portion being continuous with a second portion" refers to the first portion being directly continuous with the second portion to allow a fluid such as a liquid to flow between the first portion and the second portion or refers to the first portion being continuous with the second portion through another portion (also referred to as a third portion) to allow a fluid to flow between the first portion and the second portion. The first portion, the second portion, and the third portion herein are each a portion in which a fluid can flow, such as a flow path or a hole. The third portion may be a combination of two or more flow paths, a combination of one or more flow paths and one or more holes, or a combination of two or more holes. The flow path portion 30 is inside the first flow path device 3. In other words, for example, the flow path portion 30 is not open in either the first upper surface 3a or the first lower surface 3b. FIG. 2 illustrates the flow path portion 30 in a simplified manner.

Figure 3:
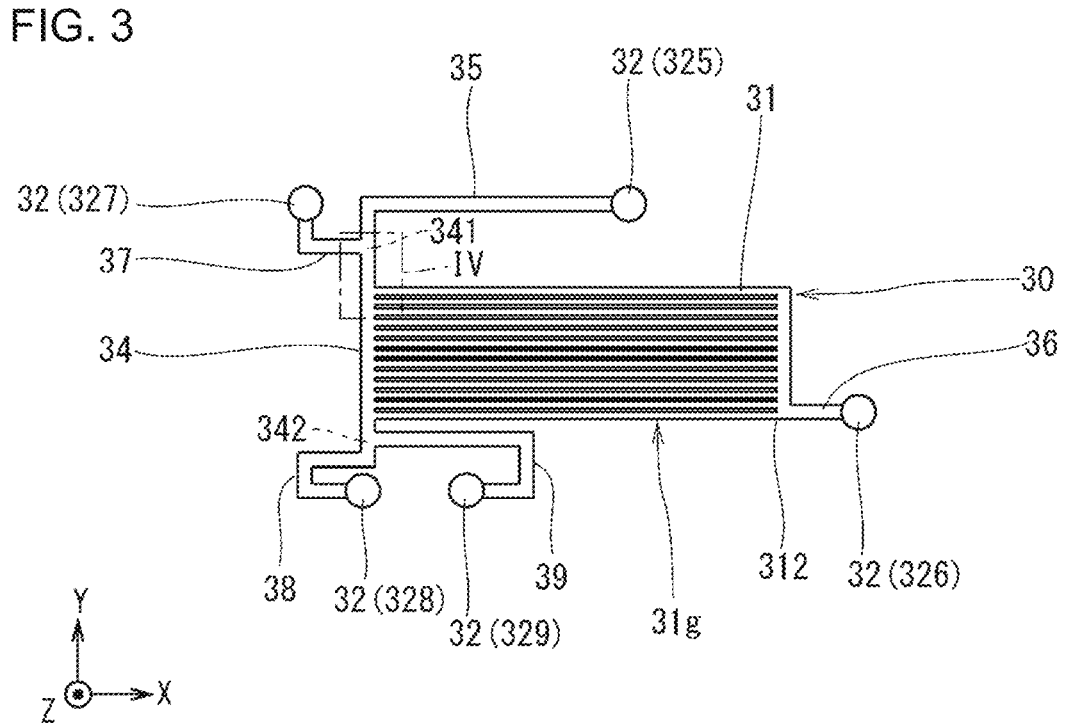
FIG. 3 is a schematic plan view of a flow path portion and multiple holes in the first flow path device, illustrating their example structures.
Figure 4:
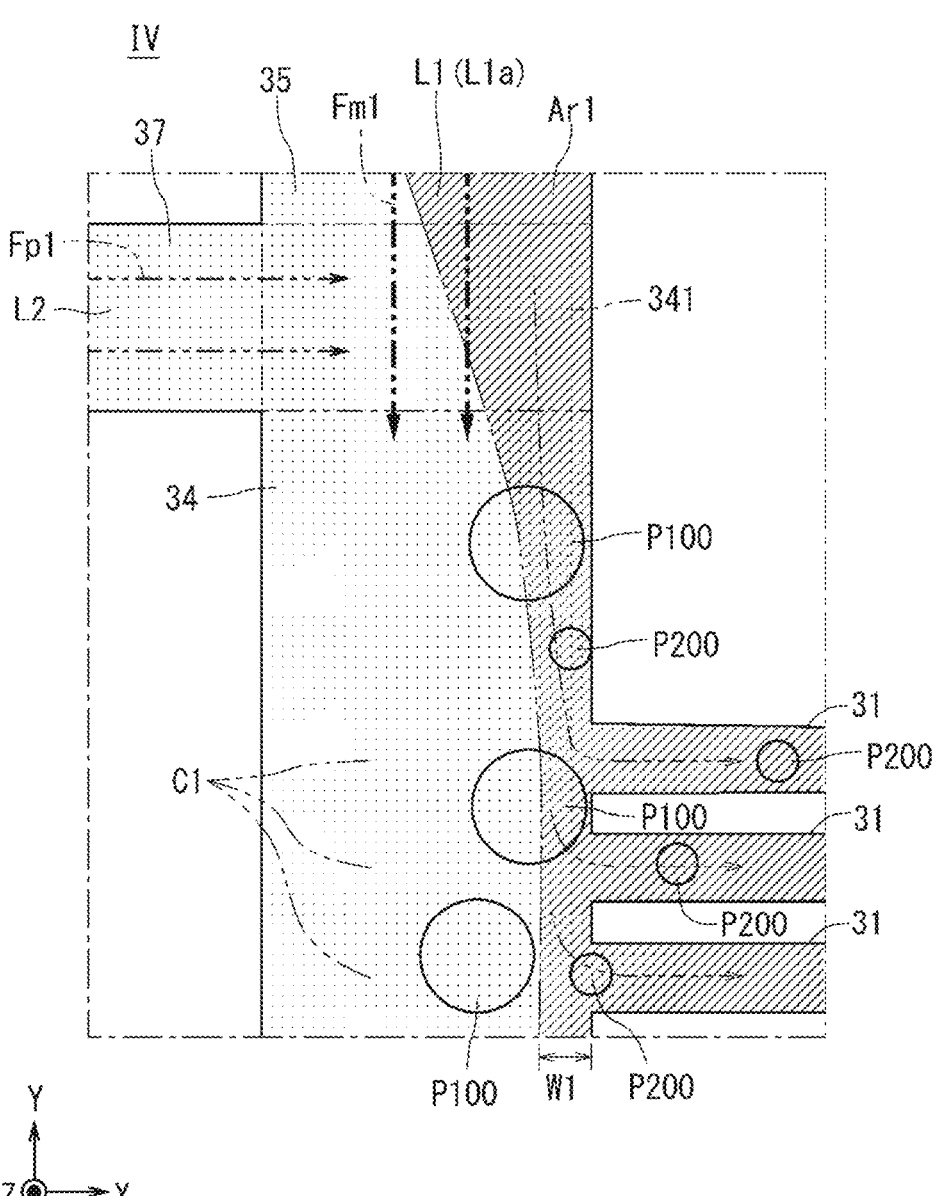
FIG. 4 is a plan view of a rectangular area IV defined by a dot-dash line in FIG. 3.

FIG. 3 is a schematic plan view of the flow path portion 30 and the multiple holes 32 in the first flow path device 3, illustrating their example structures. In FIG. 3, an outer edge of the first flow path device 3 is not illustrated, and outer edges of the flow path portion 30, two inlet holes 325 and 327, and three outlet holes 326, 328, and 329 are drawn with solid lines. FIG. 4 illustrates a part of the flow path portion 30. In FIG. 4, outer edges of a main flow path 34, multiple branch flow paths 31, and two flow paths 35 and 37 are drawn with solid lines.

The flow path portion 30 includes multiple flow paths that are grooves connected to one another and are not open in the outer surface of the first flow path device 3. The flow path portion 30 includes, for example, the main flow path 34 as a first flow path and the multiple branch flow paths 31 as second flow paths.

The main flow path 34 is, for example, a straight flow path extending in the negative Y-direction as the first direction. The main flow path 34 includes an upstream portion (also referred to as a first upstream portion) 341 and a downstream portion (also referred to as a first downstream portion) 342. The main flow path 34 extends in the negative Y-direction as the first direction from the first upstream portion 341 to the first downstream portion 342.

Each of the multiple branch flow paths 31 is, for example, connected to the main flow path 34 and is narrower than the main flow path 34. For example, the branch flow paths 31 are each open in a side surface of the main flow path 34 located in the positive X-direction as the second direction between the first upstream portion 341 and the first downstream portion 342. The negative Y-direction as the first direction and the positive X-direction as the second direction are orthogonal to each other. In other words, the main flow path 34 includes multiple portions (also referred to as connections) C1 connected to the respective branch flow paths 31. For example, the branch flow paths 31 branch from the main flow path 34 at respective different positions in the negative Y-direction as the first direction. In other words, the multiple connections C1 connected to the respective branch flow paths 31 are at respective different positions in the negative Y-direction as the first direction.

In the examples in FIGS. 1 and 3, the multiple branch flow paths 31 each extend in the positive X-direction as the second direction. In other words, the branch flow paths 31 are arranged in the negative Y-direction as the first direction. The branch flow paths 31 are included in, for example, a group 31g of branch flow paths 31 (also referred to as a branch flow path group). The branch flow paths 31 may be, for example, about ten to about several hundreds branch flow paths 31. FIGS. 1 and 3 illustrate thirteen branch flow paths 31 for convenience.

The multiple holes 32 include, for example, the inlet hole 327 as a first inlet hole, the inlet hole 325 as a second inlet hole, the outlet hole 329 as a first outlet hole, the outlet hole 326 as a second outlet hole, and the outlet hole 328 as a third outlet hole.

The inlet hole 327 is, for example, continuous with the first upstream portion 341 in the main flow path 34. For example, the inlet hole 327 is connected to the first upstream portion 341 through the flow path 37. In other words, the flow path portion 30 includes the flow path 37 as a third flow path connecting the inlet hole 327 as the first inlet hole and the first upstream portion 341. For example, the flow path 37 is wider than each of the branch flow paths 31. The inlet hole 327 has a diameter that is, for example, the same as or larger than the width of the flow path 37. In the first embodiment, the flow path 37 includes a portion connected to the first upstream portion 341 and being open in a side surface of the main flow path 34 located opposite to the positive X-direction as the second direction. In the examples in FIGS. 1 and 3, the flow path 37 is an L-shaped flow path including a portion extending from the inlet hole 327 in the negative Y-direction as the first direction and a portion extending in the positive X-direction as the second direction and connected to the first upstream portion 341. These portions are connected in the stated order. In other words, the flow path 37 extends in the negative Y-direction and then in the positive X-direction.

The inlet hole 325 is, for example, continuous with the first upstream portion 341 in the main flow path 34. For example, the inlet hole 325 is connected to the first upstream portion 341 through the flow path 35. In other words, the flow path portion 30 includes the flow path 35 as a fourth flow path connecting the inlet hole 325 as the second inlet hole and the first upstream portion 341. For example, the flow path 35 is wider than each of the branch flow paths 31. The inlet hole 325 has a diameter that is, for example, the same as or larger than the width of the flow path 35. In the first embodiment, the flow path 35 includes a portion connected to the first upstream portion 341 and extending in the negative Y-direction as the first direction. In the examples in FIGS. 1 and 3, the flow path 35 extends in the negative Y-direction as the first direction to be connected to the first upstream portion 341 in the main flow path 34. More specifically, the flow path 35 is an L-shaped flow path including a portion extending from the inlet hole 325 in the negative X-direction opposite to the second direction and a portion extending in the negative Y-direction as the first direction. These portions are connected in the stated order. In other words, the flow path 35 extends in the negative X-direction and then in the negative Y-direction.

The outlet hole 329 is, for example, continuous with the first downstream portion 342 in the main flow path 34. For example, the outlet hole 329 is connected to the first downstream portion 342 through a flow path 39. In other words, the flow path portion 30 includes the flow path 39 as a fifth flow path connecting the outlet hole 329 as the first outlet hole and the first downstream portion 342. For example, the flow path 39 is wider than each of the branch flow paths 31. The outlet hole 329 has a diameter that is, for example, the same as or larger than the width of the flow path 39. In the first embodiment, the flow path 39 includes a portion connected to the first downstream portion 342 and being open in a side surface of the first downstream portion 342 located in the positive X-direction as the second direction. In the examples in FIGS. 1 and 3, the flow path 39 is a U-shaped flow path including a portion connected to the first downstream portion 342 and extending in the positive X-direction as the second direction, a portion extending in the negative Y-direction as the first direction, and a portion extending in the negative X-direction opposite to the second direction. These portions are connected in the stated order. In other words, the flow path 39 extends in the positive X-direction, in the negative Y-direction, and then in the negative X-direction.

The outlet hole 326 is continuous with, for example, a portion (also referred to as a second downstream portion) 312 in each of the multiple branch flow paths 31 opposite to the main flow path 34. For example, the outlet hole 326 is connected to the second downstream portion 312 in each of the branch flow paths 31 through a flow path 36. In other words, the flow path portion 30 includes the flow path 36 as a sixth flow path connecting the outlet hole 326 as the second outlet hole and the second downstream portion 312 in each of the branch flow paths 31. More specifically, for example, the branch flow paths 31 are connected to the flow path 36 at respective different positions in the negative Y-direction as the first direction. For example, the flow path 36 is wider than each of the branch flow paths 31. The outlet hole 326 has a diameter that is, for example, the same as or larger than the width of the flow path 36. In the examples in FIGS. 1 and 3, the flow path 36 is an L-shaped fluid channel including a portion connected to the multiple second downstream portion 312 in the respective branch flow paths 31 and extending straight in the negative Y-direction as the first direction and a portion extending straight in the positive X-direction as the second direction. These portions are connected in the stated order. In other words, the flow path 36 extends in the negative Y-direction and then in the positive X-direction.

The outlet hole 328 is, for example, continuous with the first downstream portion 342 in the main flow path 34. For example, the outlet hole 328 is connected to the first downstream portion 342 through a flow path 38. In other words, the flow path portion 30 includes the flow path 38 as a seventh flow path connecting the outlet hole 328 as the third outlet hole and the first downstream portion 342. For example, the flow path 38 is wider than each of the branch flow paths 31. The outlet hole 328 has a diameter that is, for example, the same as or larger than the width of the flow path 38. In the first embodiment, the flow path 38 includes a portion connected to the first downstream portion 342 and extending in the negative Y-direction. In the examples in FIGS. 1 and 3, the flow path 38 includes a portion connected to the first downstream portion 342 and extending in the negative Y-direction as the first direction, a portion extending in the negative X-direction opposite to the second direction, a portion extending in the negative Y-direction as the first direction, and a portion extending in the positive X-direction as the second direction and connected to the outlet hole 328. These portions are connected in the stated order. In other words, the flow path 38 extends in the negative Y-direction, in the negative X-direction, in the negative Y-direction, and then in the positive X-direction.

In the first embodiment, for example, the two inlet holes 325 and 327 and the three outlet holes 326, 328, and 329 are each not open in the first upper surface 3a and are open in the first lower surface 3b. For example, the inlet hole 327 includes a first inlet opening 1i as a first opening that is open in the first lower surface 3b. The inlet hole 325 includes a second inlet opening 2i as a second opening that is open in the first lower surface 3b. In other words, the first flow path device 3 includes, inside the first flow path device 3, the flow path portion 30 that allows a liquid flow between the first inlet opening 1i and the second inlet opening 2i. The outlet hole 329 includes a first outlet opening 1o as a third opening that is open in the first lower surface 3b. The outlet hole 326 includes a second outlet opening 2o as a fourth opening that is open in the first lower surface 3b. The outlet hole 328 includes a third outlet opening 3o as a fifth opening that is open in the first lower surface 3b.

1-2. Overall Example Functions of First Flow Path Device

A liquid (also referred to as a first liquid, refer to FIGS. 4 and 6) L1 as a process target and a liquid (also referred to as a second liquid, refer to FIGS. 4 and 6) L2 different from the first liquid L1 are introduced into the first flow path device 3. The first flow path device 3 thus performs, for example, a process (also referred to as a particle separating process) on particles P100 and P200 of multiple types (refer to FIG. 4) contained in the first liquid L1 to separate target particles P100 of a specific type (also referred to as separating target particles) from particles P200 of another type (also referred to as non-target particles) and discharge the separating target particles P100.

The functions of the first flow path device 3 for the particle separating process are roughly described below.

The first liquid L1 containing the particles P100 and P200 of multiple types is introduced into the first flow path device 3. For example, the first flow path device 3 separates the separating target particles P100 as particles of a specific type from the non-target particles P200, and discharges the separating target particles P100. The liquid may contain particles of three or more types. In the example described below, the separating target particles P100 are of a single type, and the non-target particles P200 are of another single type.

The second liquid L2 that functions as a flow-directing liquid is introduced into the first flow path device 3 through the inlet hole 327. The first liquid L1 is introduced into the first flow path device 3 through the inlet hole 325. Specific examples and the functions of the second liquid L2 are described later.

For example, a tubular member may be externally connected to the first flow path device 3 to introduce the second liquid L2 into the first flow path device 3 through the inlet hole 327. To connect the tubular member, for example, the first lower surface 3b of the first flow path device 3 may include a cylindrical portion protruding in the negative Z-direction and surrounding the inlet hole 327 about a Z-axis as viewed in plan (hereafter, as viewed in plan in the negative Z-direction unless otherwise specified).

For example, a tubular member may be externally connected to the first flow path device 3 to introduce the first liquid L1 into the first flow path device 3 through the inlet hole 325. To connect the tubular member, for example, the first lower surface 3b of the first flow path device 3 may include a cylindrical portion protruding in the negative Z-direction and surrounding the inlet hole 325 about the Z-axis as viewed in plan.

For example, the first liquid L1 introduced into the first flow path device 3 through the inlet hole 325 flows through the flow path 35 into the first upstream portion 341 in the main flow path 34. For example, the second liquid L2 introduced into the first flow path device 3 through the inlet hole 327 flows through the flow path 37 into the first upstream portion 341 in the main flow path 34.

In FIG. 4, arrows Fp1 drawn with two-dot-dash lines indicate a direction in which the second liquid L2 flows. The direction is the positive X-direction. In FIG. 4, arrows Fm1 drawn with two-dot-dash lines thicker than the arrows Fp1 indicate a direction in which the first liquid L1 mainly flows (also referred to as a main flow) from the flow path 35 into the main flow path 34. The direction of the main flow is the negative Y-direction as the first direction. In FIG. 4, a rectangle drawn with a thin two-dot-dash line imaginarily indicates an outer edge of the first upstream portion 341.

FIG. 4 schematically illustrates the separating target particles P100 with a larger diameter than the non-target particles P200 being separated from the non-target particles P200. More specifically, for example, each of the branch flow paths 31 has a width larger than the diameter of the non-target particles P200 and smaller than the diameter of the separating target particles P100. The width of each of the branch flow paths 31 herein refers to the dimension of the branch flow path 31 in the Y-direction.

At least the main flow path 34 and the flow path 35 each have a width larger than the diameter of the separating target particles P100 and the diameter of the non-target particles P200. The width of the main flow path 34 herein refers to the dimension of the main flow path 34 in the X-direction orthogonal to the negative Y-direction as the first direction. The width of the flow path 35 refers to the dimension of the flow path 35 in the X-direction for its portion near the main flow path 34. The width of the flow path 35 refers to the dimension of the flow path 35 in the Y-direction for its portion extending in the negative X-direction.

The non-target particles P200 move in the negative Y-direction as the first direction in the main flow path 34 and receive a directing force in the positive X-direction. Most of the non-target particles P200 are thus each introduced into any of the branch flow paths 31. Most of the non-target particles P200 each sequentially flow through any of the branch flow paths 31 and the flow path 36 and are discharged out of the first flow path device 3 through the outlet hole 326. In this example, the branch flow paths 31 connected to the main flow path 34 each have a cross-sectional area and a length adjusted to cause each of the non-target particles P200 to flow from the main flow path 34 into any of the branch flow paths 31 and to be separated from the separating target particles P100. The non-target particles P200 discharged out of the first flow path device 3 through the outlet hole 326 may undergo, for example, a specific process in another device directly connected to the outlet hole 326 or connected using another member such as a tube, or may be simply collected. The non-target particles P200 discharged out of the first flow path device 3 through the outlet hole 326 may be, for example, directly discarded or discarded through another member such as a tube.

The separating target particles P100 move in the negative Y-direction as the first direction in the main flow path 34 substantially without being introduced into the multiple branch flow paths 31. Most of the separating target particles P100 sequentially flow through the main flow path 34 and the flow path 39 and are discharged out of the first flow path device 3 through the outlet hole 329. In this example, the flow path 39 has a width larger than the size of the separating target particles P100. The separating target particles P100 reaching the first downstream portion 342 flow into the flow path 39, rather than into the flow path 38, under the same force as for each of the non-target particles P200 flowing into any of the branch flow paths 31 from the main flow path 34. The separating target particles P100 discharged out of the first flow path device 3 through the outlet hole 329 may undergo, for example, a specific process in another device directly connected to the outlet hole 329 or connected using another member such as a tube, or may be simply collected.

A component (also referred to as a remaining component) of the first liquid L1 other than the non-target particles P200 each flowing into any of the branch flow paths 31 and the separating target particles P100 flowing into the flow path 39 flows into the flow path 38. The remaining component flows through the flow path 38 and is discharged through the outlet hole 328. The remaining component discharged out of the first flow path device 3 through the outlet hole 328 may undergo, for example, a specific process in another device directly connected to the outlet hole 328 or connected using another member such as a tube, or may be simply collected. The remaining component discharged out of the first flow path device 3 through the outlet hole 328 may be, for example, directly discarded or discarded through another member such as a tube.

In the first embodiment, the first liquid L1 is directed to the branch flow paths 31 using a flow (also referred to as a fluid-drawing flow). The fluid-drawing flow may facilitate separating of the separating target particles P100 from the non-target particles P200 using the main flow path 34 and the multiple branch flow paths 31. The fluid-drawing flow is indicated by an area Ar1 hatched with diagonal lines from the lower left to the upper right in FIG. 4. The state of the fluid-drawing flow indicated by the area Ar1 in FIG. 4 is a mere example and may be changed based on the relationship between the flow velocity as well as the flow rate of the first liquid L1 introduced into the main flow path 34 through the flow path 35 and the flow velocity as well as the flow rate of the second liquid L2 introduced into the first upstream portion 341 in the main flow path 34 through the flow path 37. The area Ar1 may be adjusted as appropriate to efficiently separate the separating target particles P100 and the non-target particles P200 from the first liquid L1. The second liquid L2 directs the first liquid L1 toward the multiple branch flow paths 31 in the positive X-direction from a position opposite to the multiple branch flow paths 31. The second liquid L2 may facilitate creation of the fluid-drawing flow.

As described above, the main flow path 34 extends in the negative Y-direction as the first direction in this example. The flow path 35 includes a portion connected to the first upstream portion 341 and extending in the negative Y-direction as the first direction. The multiple branch flow paths 31 are each open in the side surface of the main flow path 34 located in the positive X-direction as the second direction between the first upstream portion 341 and the first downstream portion 342. The flow path 37 is open in a side surface of the first upstream portion 341 in the main flow path 34 located in the negative X-direction opposite to the second direction. Thus, for example, with the second liquid L2 being fed into the main flow path 34 through the inlet hole 327, the first liquid L1 containing multiple types of particles is fed into the main flow path 34 through the inlet hole 325 to generate a liquid flow that directs the particles of multiple types toward the branch flow paths 31 in the main flow path 34. This allows, for example, among the particles of multiple types, the non-target particles P200 with a smaller diameter than the width of each of the branch flow paths 31 to flow more easily into the branch flow paths 31. Thus, for example, among the particles of multiple types in the first liquid L1, the separating target particles P100 with a larger diameter than the width of each of the branch flow paths 31 may be easily separated from the non-target particles P200 with a smaller diameter than the width of each of the branch flow paths 31.

In the first embodiment, as described above, the flow path 39 includes a portion connected to the first downstream portion 342 in the main flow path 34 and being open in the side surface of the first downstream portion 342 in the positive X-direction as the second direction. Thus, the fluid-drawing flow in the main flow path 34 allows, for example, the separating target particles P100 with a larger diameter than the width of each of the branch flow paths 31 to easily flow into the flow path 39. This allows, for example, the separating target particles P100 to flow through the flow path 39 and to be easily discharged out of the first flow path device 3 through the outlet hole 329. Thus, for example, among the particles of multiple types in the first liquid L1, the separating target particles P100 with a larger diameter than the width of each of the branch flow paths 31 may be easily separated from the non-target particles P200 with a smaller diameter than the width of each of the branch flow paths 31.

In FIG. 4, the fluid-drawing flow in the main flow path 34 has a width W1 in an area near the main flow path 34 branched to the multiple branch flow paths 31. In this example, the width of the fluid-drawing flow in the main flow path 34 refers to the dimension of the fluid-drawing flow in the X-direction. The width W1 may be set by, for example, adjusting the cross-sectional areas and the lengths of the main flow path 34 and the branch flow paths 31 as well as by the flow rates of the first liquid L1 and the second liquid L2.

At the width W1 illustrated in FIG. 4, the area Ar1 of the fluid-drawing flow does not include the center of gravity of each of the separating target particles P100 and includes the center of gravity of each of the non-target particles P200.

The first liquid L1 is, for example, blood. Blood is a liquid containing particles of multiple types. In this case, for example, the separating target particles P100 are white blood cells, and the non-target particles P200 are red blood cells. The specific process on the separating target particles P100 is, for example, to count white blood cells. The remaining component flowing into the flow path 38 and discharged out of the first flow path device 3 through the outlet hole 328 is, for example, blood plasma. In this case, the second liquid L2 is, for example, saline. More specifically, the second liquid L2 is, for example, phosphate-buffered saline (PBS). The second liquid L2 may be a liquid of PBS containing other elements to allow the second liquid L2 to function appropriately for the purpose of using the first flow path device 3. The other elements may be, for example, ethylenediaminetetraacetic acid (EDTA) as a second element and bovine serum albumin (BSA) as a third element. In this example, the main flow path 34 and the branch flow paths 31 included in the flow path portion 30 function as flow paths to separate particles in blood. In other words, the flow path portion 30 includes the main flow path 34 and the branch flow paths 31 to separate particles in blood.

A red blood cell has the center of gravity at, for example, about 2 to 2.5 micrometers ($\mu$m) from its outer rim. A red blood cell has a maximum diameter of, for example, about 6 to 8 $\mu$m. A white blood cell has the center of gravity at, for example, about 5 to 10 $\mu$m from its outer rim. A white blood cell has a maximum diameter of, for example, about 10 to 30 $\mu$m. To effectively separate red blood cells and white blood cells in blood, the fluid-drawing flow has the width W1 of about 2 to 15 $\mu$m.

The main flow path 34 has an imaginary cross-sectional area of, for example, about 300 to 1000 square micrometers ($\mu$m$^2$) along an XZ plane. The main flow path 34 has a length of, for example, about 0.5 to 20 mm in the Y-direction. Each of the branch flow paths 31 has an imaginary cross-sectional area of, for example, about 100 to 500 $\mu$m$^2$ along a YZ plane. Each of the branch flow paths 31 has a length of, for example, about 3 to 25 mm in the X-direction. The first liquid L1 in the main flow path 34 flowing in the negative Y-direction as the first direction has a flow velocity of, for example, about 0.2 to 5 meters per second (m/s). The liquid in the main flow path 34 has a flow rate per unit time of, for example, about 0.1 to 5 microliters per second ($\mu$l/s).

The material for the first flow path device 3 is, for example, a resin such as polydimethylsiloxane (PDMS). PDMS is, for example, highly transferable in resin molding using a mold. A material being transferrable refers to a material being capable of forming, on a resin-molded product, fine protrusions and recesses corresponding to a fine pattern on the mold.

The first flow path device 3 may be manufactured by, for example, bonding a first portion that is a plate including fine protrusions and recesses on one surface corresponding to the pattern of the flow path portion 30 and a second portion that is a plate including five through-holes corresponding to the two inlet holes 325 and 327 and the three outlet holes 326, 328, and 329 with one surface of the second portion covering the fine protrusions and recesses on the first portion. The first portion including the fine protrusions and recesses on one surface may be manufactured by, for example, resin molding. The second portion including the five through-holes may be manufactured by, for example, resin molding or by punching five through-holes in a member being a flat plate manufactured by resin molding. The first portion and the second portion may be bonded together without an adhesive and may be bonded by, for example, surface modification of one surface of the first portion and one surface of the second portion or by contact between one surface of the first portion and one surface of the second portion. The surface modification may be performed by, for example, irradiation of oxygen plasma or irradiation of ultraviolet (UV) light using an excimer lamp. For example, with the one surface of the first portion and the one surface of the second portion being made of the same type of resin, the bonding strength between the one surface of the first portion and the one surface of the second portion in surface modification may be increased.

1-3. Example Method for Introducing Liquid into First Flow Path Device

Figure 5:
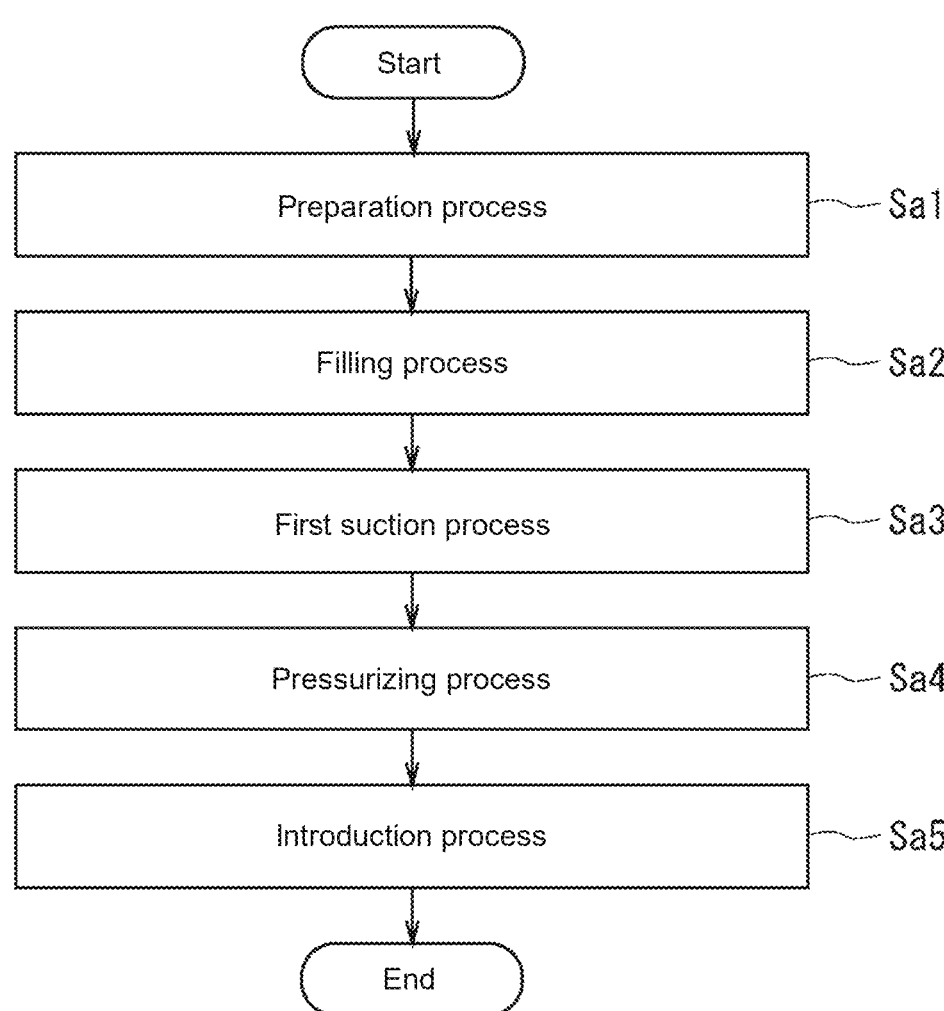
FIG. 5 is a flowchart of example processing with a method for introducing a liquid into the first flow path device according to the first embodiment.

An example method for introducing the first liquid L1 and the second liquid L2 into the first flow path device 3 will now be described. FIG. 5 is a flowchart of example processing with a method for introducing a liquid into the first flow path device 3.

In this example, as illustrated in FIG. 5, a preparation process in step Sa1, a filling process in step Sa2, a first suction process in step Sa3, a pressurizing process in step Sa4, and an introduction process in step Sa5 are performed in this order. In other words, the method for introducing a liquid into the first flow path device 3 includes the preparation process, the filling process, the first suction process, the pressurizing process, and the introduction process.

FIGS. 6 to 10 are each a conceptual diagram of the first flow path device 3 and components, illustrating their example states in the corresponding process. The components include a switcher 5, a liquid storage 6, a suction-discharge unit 7, and a liquid feeder 4. In FIGS. 6 to 10, the area with the first liquid L1 is hatched with diagonal lines from the lower left to the upper right, and the area with the second liquid L2 is hatched with a dot pattern. In FIGS. 6 to 10, the upper surface of the liquid is schematically drawn with thin two-dot-dash lines, and the direction in which the liquid flows is schematically drawn with thin two-dot-dash arrows. To facilitate understanding of the connection states and the operation states of the components, FIGS. 6 to 10 illustrate the components such as the switcher 5, the liquid storage 6, the suction-discharge unit 7, and the liquid feeder 4 with their vertical direction aligned with the vertical direction in the figures (the upward direction in the figures is the positive Z-direction, and the downward direction in the figures is the negative Z-direction), and illustrate the multiple flow paths and the multiple holes in the first flow path device 3 with their upward direction (positive Z-direction) aligned with the frontward direction in the figures for convenience.

Preparation Process

In the preparation process in step Sa1, a connection is established between the first flow path device 3 and the switcher 5 to allow a liquid flow between the first flow path device 3 and the switcher 5. A connection is established between the switcher 5 and the internal space of the liquid storage 6 to allow a liquid flow between the switcher 5 and the internal space. A connection is established between the suction-discharge unit 7 and the switcher 5 to allow a liquid flow between the suction-discharge unit 7 and the switcher 5. A connection is established between the liquid feeder 4 and the first flow path device 3 to allow a liquid flow between the liquid feeder 4 and the first flow path device 3.

Figure 6:
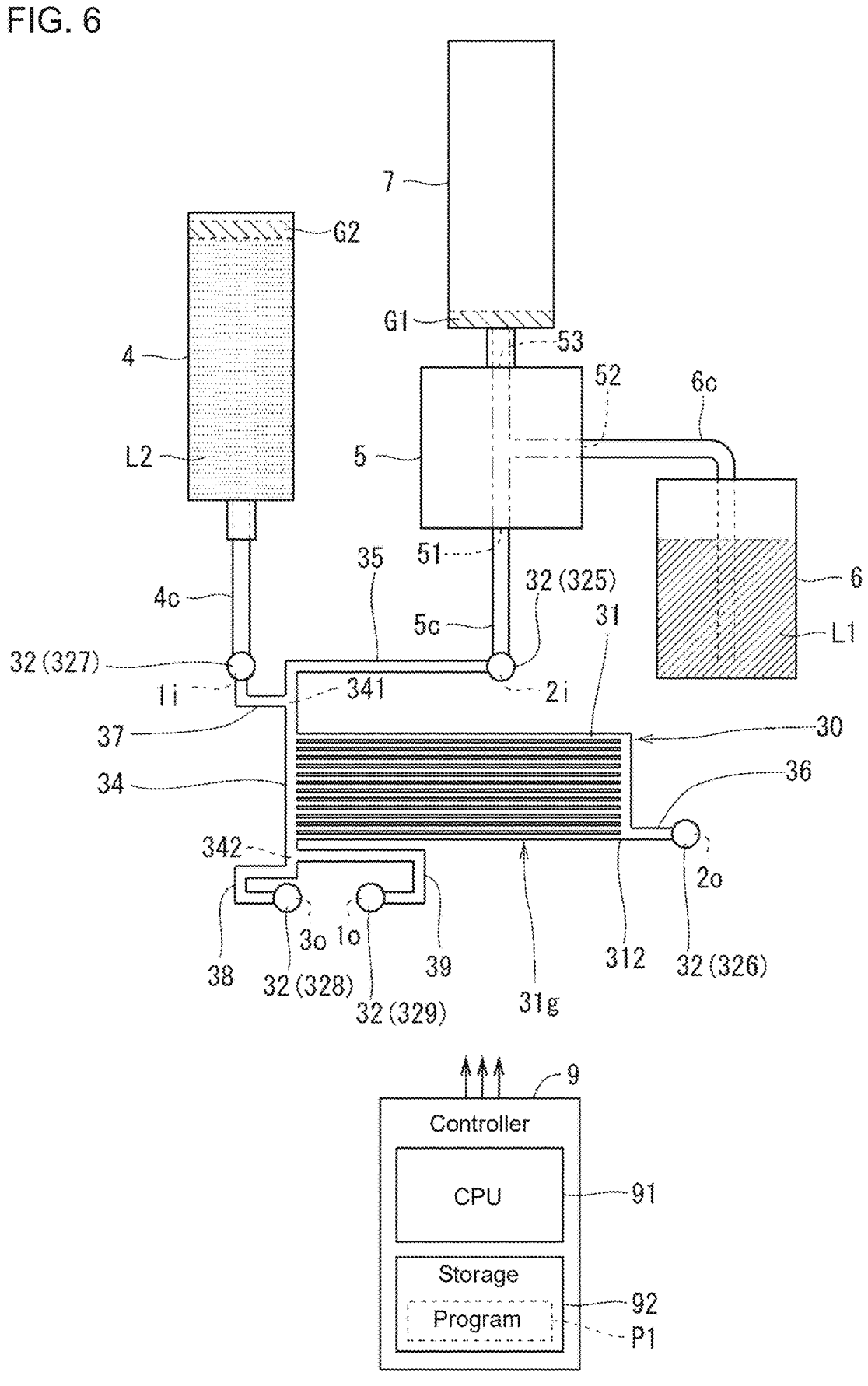
FIG. 6 is a conceptual diagram of the first flow path device and components, illustrating their example connection states in a preparation process.

FIG. 6 is a conceptual diagram of the first flow path device 3 and the components, illustrating their example connection states in the preparation process.

The switcher 5 includes a first port 51, a second port 52, and a third port 53. The switcher 5 can be selectively set to a state allowing a liquid flow between any two of the three ports, or specifically the first port 51, the second port 52, and the third port 53. More specifically, the switcher 5 can be selectively set to one of a first state, a second state, or a third state. The first state is a state allowing a liquid flow between the first port 51 and the second port 52. The second state is a state allowing a liquid flow between the second port 52 and the third port 53. The third state is a state allowing a liquid flow between the first port 51 and the third port 53. In other words, the switcher 5 can switch the liquid flow in the switcher 5 between the first state, the second state, and the third state.

The switcher 5 is, for example, a three-way valve referred to as a T-port valve. The T-port, three-way valve may be a three-way stopcock. In the example described below, the switcher 5 is a T-port, three-way valve. In this case, the first state is a state allowing a liquid flow through an L-shaped flow path between the first port 51 and the second port 52. The second state is a state allowing a liquid flow through an L-shaped flow path between the second port 52 and the third port 53. The third state is a state allowing a liquid flow through a straight flow path between the first port 51 and the third port 53. Switching with the three-way valve between the first state, the second state, and the third state may be performed by moving, for example, a cock manually or automatically. The switcher 5 may switch between the first state, the second state, and the third state using any of various components. The various components may include, for example, an electromagnetic valve, a piezoelectric member (e.g., a piezoelectric device), a pinch valve, or a component for opening or closing the flow path using air pressure. The pinch valve is, for example, a solenoid valve that can directly compress a soft tube, such as a silicone tube, to close the flow path.

In FIGS. 6 to 10, outer edges of the flow paths that can connect the first port 51, the second port 52, and the third port 53 in the switcher 5 to each other are schematically drawn with two-dot-dash lines. In FIGS. 6 to 10, the L-shaped flow path between the first port 51 and the second port 52 having solid line outer edges schematically indicates the first state allowing a liquid flow through the L-shaped flow path between the first port 51 and the second port 52. The L-shaped flow path between the second port 52 and the third port 53 having solid line outer edges schematically indicates the second state allowing a liquid flow through the L-shaped flow path between the second port 52 and the third port 53. The straight flow path between the first port 51 and the third port 53 having solid line outer edges schematically indicates the third state allowing a liquid flow through the straight flow path between the first port 51 and the third port 53.

The operation of the switcher 5 may be controlled in response to, for example, a signal from a controller 9. In this case, the controller 9 controls, for example, switching of the state of the switcher 5 between the first state, the second state, and the third.

In the preparation process in the first embodiment, a connection is established between the first flow path device 3 and the switcher 5 to allow a liquid flow between the second inlet opening 2*i* in the first flow path device 3 and the first port 51 in the switcher 5. The second inlet opening 2*i* and the first port 51 are connected to each other with, for example, a flow path (also referred to as a first connection flow path) 5*c* to allow a liquid flow between the second inlet opening 2*i* and the first port 51. The first connection flow path 5*c* has one end (also referred to as a first end) connected to the second inlet opening 2*i*. The first connection flow path 5*c* has an end (also referred to as a second end) opposite to the first end and connected to the first port 51. The first connection flow path 5*c* is, for example, a tubular member made of a resin or a metal. The tubular member made of a resin is, for example, a flexible tube. The first connection flow path 5*c* may include, for example, one or more members or devices including a flow path inside. The first connection flow path 5*c* may be straight or may include a curve, a bend, or a twist. The second inlet opening 2*i* and the first port 51 may be, for example, directly connected to each other without the first connection flow path 5*c*.

The liquid storage 6 includes an internal space storing the first liquid L1. For example, the liquid storage 6 includes a hollow as the internal space that is open upward. The liquid storage 6 is, for example, a bottomed member such as a vial or a tank. Examples of the vial include a small container and a small bottle made of glass or plastic.

In the preparation process in the first embodiment, a connection is established between the internal space of the liquid storage 6 and the second port 52 in the switcher 5 to allow a liquid flow between the internal space and the second port 52. The second port 52 and the liquid storage 6 are connected to each other with, for example, a flow path (also referred to as a second connection flow path) 6*c* to allow a liquid flow between the second port 52 and the liquid storage 6. The second connection flow path 6*c* has one end (also referred to as a third end) connected to the second port 52. The second connection flow path 6*c* has an end (also referred to as a fourth end) opposite to the third end and located in the internal space of the liquid storage 6. For example, the second connection flow path 6*c* extends through an upper opening of the liquid storage 6 to the internal space of the liquid storage 6. In this case, for example, the fourth end and its adjacent portion of the second connection flow path 6*c* are placed in the first liquid L1 stored in the internal space of the liquid storage 6. For example, the fourth end is located near the bottom of the internal space of the liquid storage 6. In the examples in FIGS. 6 to 10, an outer edge of the portion of the second connection flow path 6*c* located in the internal space of the liquid storage 6 is drawn with thin dashed lines. The second connection flow path 6*c* is, for example, a tubular member made of a resin or a metal. The second connection flow path 6*c* may include, for example, one or more members or devices including a flow path inside. The second connection flow path 6*c* may be straight or may include a curve, a bend, or a twist.

The suction-discharge unit 7 can suck and discharge a liquid. For example, the suction-discharge unit 7 sucks a liquid, temporarily stores the sucked liquid into its reservoir, and then pressurizes the reservoir to discharge the liquid from the reservoir. The suction-discharge unit 7 is, for example, a member or a device that can stably suck a liquid at a predetermined pressure and a predetermined flow velocity and can then stably discharge and feed the liquid at a predetermined pressure and a predetermined flow velocity. The suction-discharge unit 7 is, for example, any of various pumps, such as a syringe pump. The suction-discharge unit 7 may be, for example, a tank device that can suck a liquid into the reservoir under an external tensile force and discharge the liquid from the reservoir under an external pressing force.

In the examples in FIGS. 6 to 10, the suction-discharge unit 7 is a syringe pump. The area with a gasket (also referred to as a first gasket) G1 in the syringe pump is hatched with widely spaced diagonal lines from the lower right to the upper left. An outer edge of the first gasket G1 is schematically indicated by dashed lines. A component such as a plunger for pushing and pulling the first gasket G1 is not illustrated.

The operation of the suction-discharge unit 7 may be controlled in response to, for example, a signal from the controller 9. In this case, the controller 9 controls, for example, the suction and discharge of a liquid with the suction-discharge unit 7. The controller 9 may control, for example, the suction amount per unit time (also referred to as a suction rate) of a liquid sucked by the suction-discharge unit 7 and the discharge amount per unit time (also referred to as a discharge rate) of a liquid discharged by the suction-discharge unit 7.

In the preparation process in the first embodiment, a connection is established between the suction-discharge unit 7 and the third port 53 in the switcher 5 to allow a liquid flow between the suction-discharge unit 7 and the third port 53. The suction-discharge unit 7 and the third port 53 may be, for example, directly connected or connected through a connection flow path to allow a liquid flow between the suction-discharge unit 7 and the third port 53. The connection flow path may be, for example, a tubular member made of a resin or a metal, or may include one or more members or devices including a flow path inside. More specifically, for example, the suction-discharge unit 7 includes an opening for sucking and discharging a liquid, and the opening is connected to the third port 53 directly or with one or more members or devices between the opening and the third port 53. When, for example, the suction-discharge unit 7 is a syringe pump, a tube end of the syringe pump for sucking and discharging a liquid is connected to the third port 53 directly or with one or more members or devices between the tube end and the third port 53. For example, the opening of the suction-discharge unit 7 for sucking and discharging a liquid is located in a lower portion of the suction-discharge unit 7.

The liquid feeder 4 can feed the second liquid L2. For example, the liquid feeder 4 stores the second liquid L2 and can discharge the stored second liquid L2. The liquid feeder 4 is, for example, a member or a device that can stably feed a liquid at a predetermined pressure and a predetermined flow velocity. The liquid feeder 4 is, for example, any of various pumps, such as a syringe pump or a plunger pump.

In the examples in FIGS. 6 to 10, the liquid feeder 4 is a syringe pump. The area with a gasket (also referred to as a second gasket) G2 in the syringe pump is hatched with widely spaced diagonal lines from the lower right to the upper left. An outer edge of the second gasket G2 is schematically indicated by dashed lines. A component such as a plunger for pushing and pulling the second gasket G2 is not illustrated.

The operation of the liquid feeder 4 may be controlled in response to, for example, a signal from the controller 9. In this case, the controller 9 controls, for example, the feeding of a liquid with the liquid feeder 4. The controller 9 may control, for example, the feed amount per unit time (also referred to as a feed rate) of the liquid fed from the liquid feeder 4.

In the preparation process in the first embodiment, a connection is established between the liquid feeder 4 and the first inlet opening 1*i* in the first flow path device 3 to allow a liquid flow between the liquid feeder 4 and the first inlet opening 1*i*. The liquid feeder 4 and the first inlet opening 1*i* in the first flow path device 3 are connected to each other with, for example, a flow path (also referred to as a third connection flow path) 4*c* to allow a liquid flow between the liquid feeder 4 and the first inlet opening 1*i*. The third connection flow path 4*c* has one end (also referred to as a fifth end) connected to the liquid feeder 4. The third connection flow path 4*c* has an end (also referred to as a sixth end) opposite to the fifth end and connected to the first inlet opening 1*i*. The third connection flow path 4*c* is, for example, a tubular member made of a resin or a metal. The third connection flow path 4*c* may include, for example, one or more members or devices including a flow path inside. The third connection flow path 4*c* may be straight or may include a curve, a bend, or a twist. When, for example, the liquid feeder 4 is a syringe pump, the tube end of the syringe pump for sucking and discharging a liquid is connected to the fifth end of the third connection flow path 4*c*. The liquid feeder 4 and the first inlet opening 1*i* may be, for example, directly connected to each other without the third connection flow path 4*c*.

The controller 9 controls, for example, the operations of the components such as the switcher 5, the suction-discharge unit 7, and the liquid feeder 4. The controller 9 may be, for example, a computer or a control circuit. The controller 9 includes at least one processor that performs control and processing for implementing various functions, as described in more detail below.

In various embodiments, the at least one processor may be a single integrated circuit (IC), or multiple ICs, multiple discrete circuits, or both these circuits connected to one another for mutual communication. The at least one processor may be implemented using various known techniques.

In one embodiment, the processor includes one or more circuits or units that perform one or more data computation procedures or processes by, for example, executing instructions stored in an associated memory. In another embodiment, the processor may be firmware (e.g., a discrete logic component) to perform one or more data computation procedures or processes.

In various embodiments, the processor includes one or more processors, controllers, microprocessors, microcontrollers, application-specific integrated circuits (ASICs), digital signal processors, programmable logic devices, field programmable gate arrays, combinations of any of these devices or configurations, or combinations of other known devices and configurations. The processor may perform the functions described below.

In an example of the first embodiment, the controller 9 includes a central processing unit (CPU) 91 and a storage 92. The storage 92 includes, for example, non-transitory recording media readable by the CPU 91, such as a read-only memory (ROM) and a random-access memory (RAM). The storage 92 stores, for example, a program P1 for controlling the liquid feeder 4 and the suction-discharge unit 7. Various functions of the controller 9 are implemented by the CPU 91 executing the program P1 in the storage 92.

Note that the configuration of the controller 9 is not limited to the above example. For example, the controller 9 may include multiple CPUs 91. The controller 9 may also include at least one digital signal processor (DSP). The functions of the controller 9 may be implemented entirely or partially by a hardware circuit, without using software to implement the functions. The storage 92 may also include a non-transitory computer-readable recording medium other than a ROM and a RAM. The storage 92 may include, for example, a small hard disk drive, a solid-state drive (SSD), or both these drives.

Filling Process

In the filling process in step Sa2, the switcher 5 is set to the first state allowing a liquid flow between the first port 51 and the second port 52. In this state, the liquid feeder 4 feeds the second liquid L2 to fill, with the second liquid L2, the flow path from the liquid feeder 4 through the first inlet opening 1*i*, the flow path portion 30, the second inlet opening 2*i*, the first port 51, and the second port 52 to the liquid storage 6.

Figure 7:
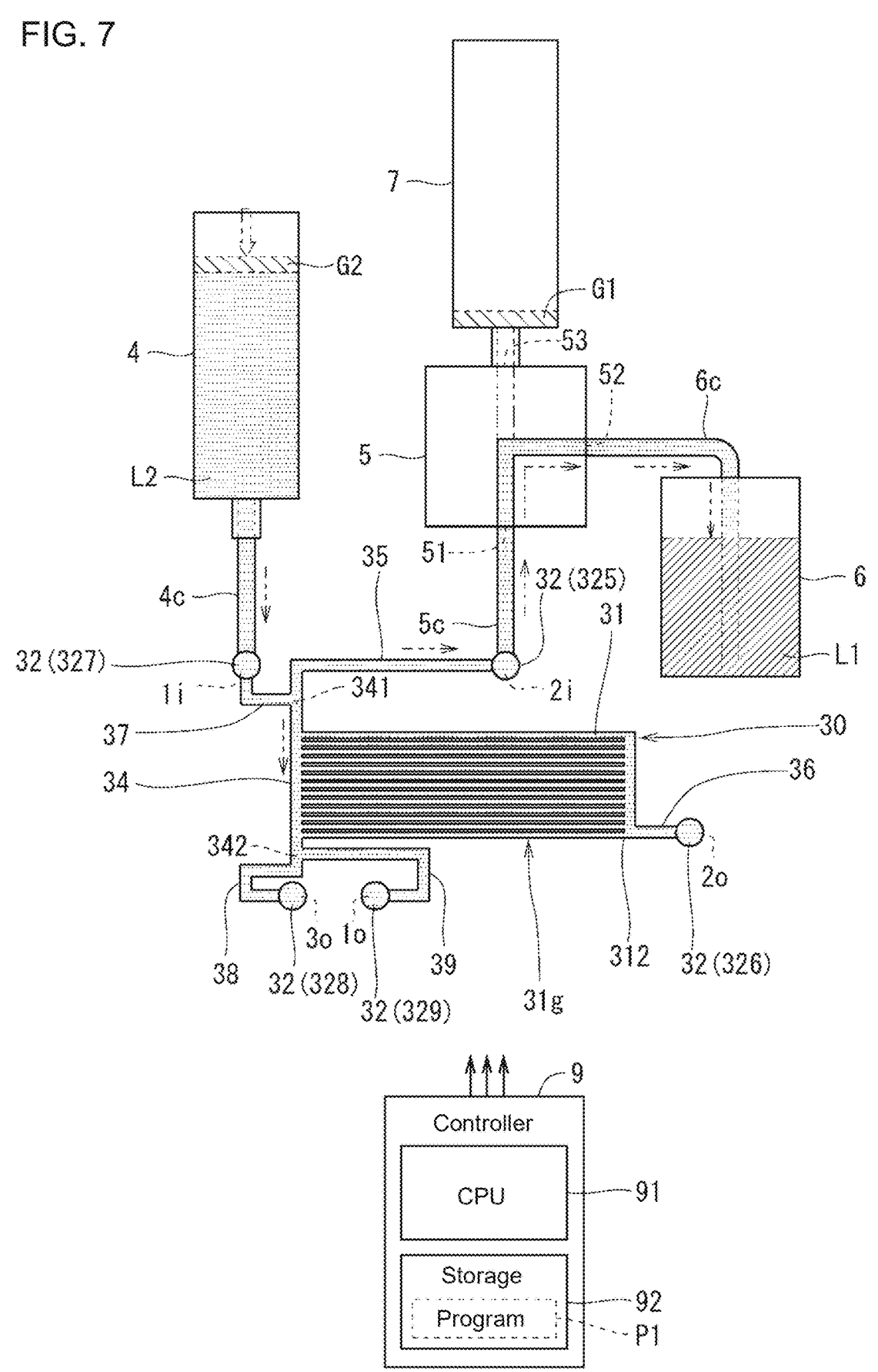
FIG. 7 is a conceptual diagram of the first flow path device and the components, illustrating their example states in a filling process.

FIG. 7 is a conceptual diagram of the first flow path device 3 and the components, illustrating their example states in the filling process. In FIG. 7, the two-dot-dash outlined arrow indicates the direction in which the second gasket G2 is pushed.

In the filling process, as illustrated in FIG. 7, an operation is started for filling the flow path portion 30 in the first flow path device 3 with the second liquid L2 fed from the liquid feeder 4. For example, an operation is started for filling the flow path portion 30 with the second liquid L2 discharged from the liquid feeder 4 through the third connection flow path 4*c*, the first inlet opening 1*i*, and the inlet hole 327. For example, the second liquid L2 is fed from the first inlet opening 1*i* through the inlet hole 327 and the flow path 37 to the first upstream portion 341, and flows from the first upstream portion 341 into the flow path 35 and also from the first upstream portion 341 toward the first downstream portion 342 in the main flow path 34. The second liquid L2 flows through the flow path 35 and the inlet hole 325 toward the second inlet opening 2*i*, flows from the main flow path 34 through the multiple branch flow paths 31, the flow path 36, and the outlet hole 326 toward the second outlet opening 2*o*, flows from the main flow path 34 through the flow path 38 and the outlet hole 328 toward the third outlet opening 30, and flows from the main flow path 34 through the flow path 39 and the outlet hole 329 toward the first outlet opening 1*o*.

In this example, the second liquid L2 flowing through the flow path 35 and the inlet hole 325 toward the second inlet opening 2*i* fills the flow path 35 and the inlet hole 325 and overflows the first flow path device 3 through the second inlet opening 2*i*. The second liquid L2 overflowing the first flow path device 3 through the second inlet opening 2*i* flows through the first connection flow path 5*c*, the first port 51, the second port 52, and the second connection flow path 6*c* and reaches the liquid storage 6. For example, the second liquid L2 flows to a portion of the second connection flow path 6*c* located between the opening of the liquid storage 6 and the surface of the first liquid L1. In this state, the switcher 5 is set to, for example, the second state allowing a liquid flow between the second port 52 and the third port 53 to stop the flow of the second liquid L2 through the second inlet opening 2*i* toward the liquid storage 6. In other words, the filling process ends. This operation reduces waste liquid resulting from wasteful discharge of the second liquid L2 when, for example, the flow path from the liquid feeder 4 through the first inlet opening 1*i*, the second inlet opening 2*i*, and the switcher 5 to the liquid storage 6 is filled with the second liquid L2. This can reduce waste liquid resulting from, for example, wasteful discharge of the second liquid L2. With the reduced waste of the second liquid L2, for example, the second liquid L2 can be prepared at lower costs for the various processes performed with the first flow path device 3.

In the filling process, for example, air contained in the flow path from the first inlet opening 1*i* through the second inlet opening 2*i* to the liquid storage 6 is pushed into the first liquid L1 stored in the liquid storage 6. The air pushed into the first liquid L1 floats in the first liquid L1 in the liquid storage 6.

For example, after the filling process ends, the liquid feeder 4 continues feeding the second liquid L2 through the third connection flow path 4*c* and the first inlet opening 1*i* to the flow path portion 30 in the first flow path device 3. This causes the flow path portion 30, the outlet hole 326, the outlet hole 328, and the outlet hole 329 to be filled with the second liquid L2. For example, after the second liquid L2 fills the flow path portion 30, the outlet hole 326, the outlet hole 328, and the outlet hole 329, the second liquid L2 is fed in a decreased feed amount per unit time (feed rate) from the liquid feeder 4 through the first inlet opening 1*i* to the flow path portion 30.

First Suction Process

In the first suction process in step Sa3, the switcher 5 is set to the second state allowing a liquid flow between the second port 52 and the third port 53. In this state, the suction-discharge unit 7 sucks the first liquid L1 from the liquid storage 6 through the second port 52 and the third port 53 into the suction-discharge unit 7.

Figure 8:
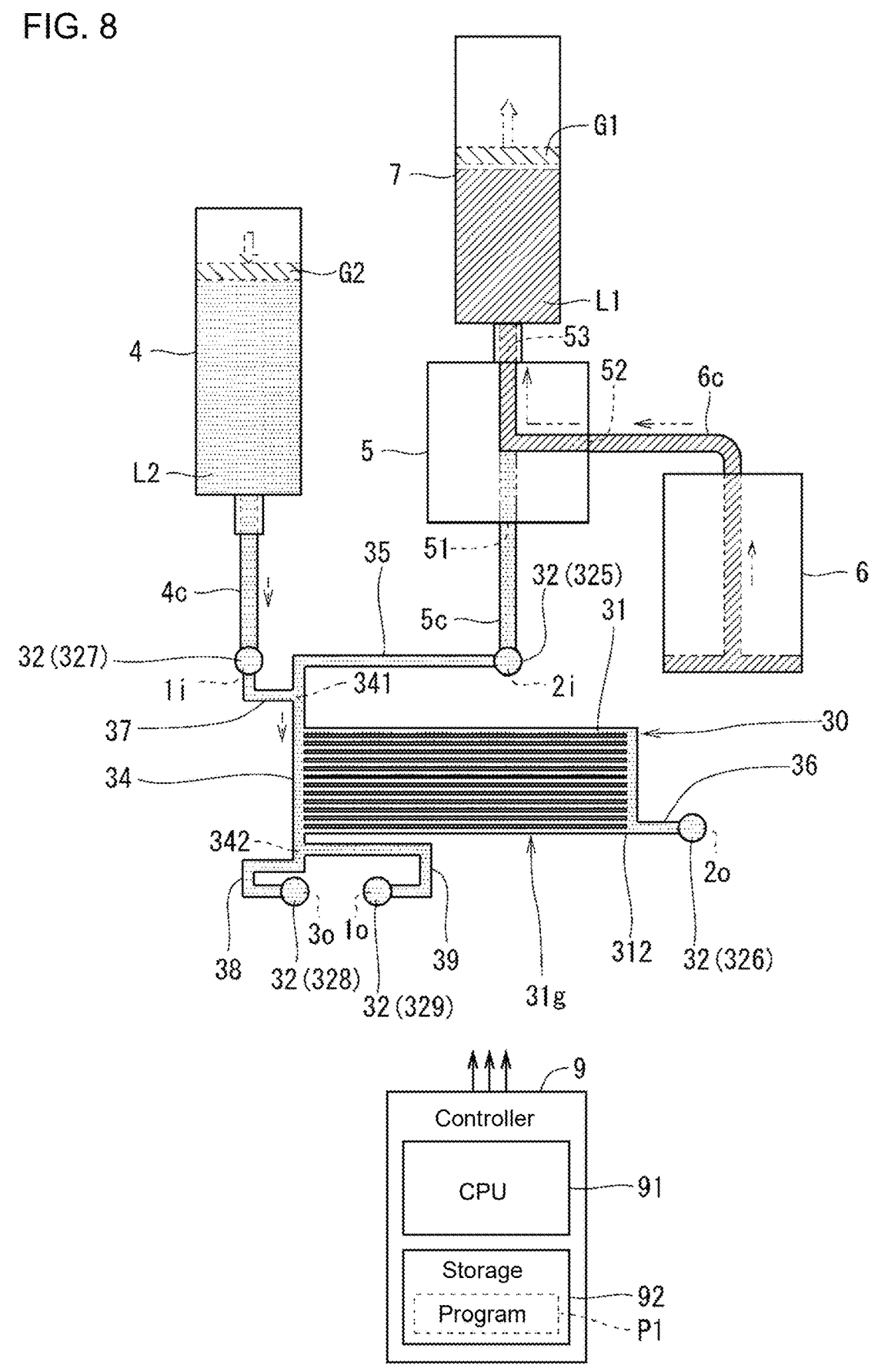
FIG. 8 is a conceptual diagram of the first flow path device and the components, illustrating their example states in a first suction process.

FIG. 8 is a conceptual diagram of the first flow path device 3 and the components, illustrating their example states in the first suction process. In FIG. 8, the two-dot-dash outlined arrow indicates each of the direction in which the first gasket G1 is pulled and the direction in which the second gasket G2 is pushed.

In the first suction process, as illustrated in FIG. 8, the first liquid L1 is sucked into the suction-discharge unit 7 from the liquid storage 6. For example, the first liquid L1 stored in the liquid storage 6 is sucked by the suction-discharge unit 7 through the second connection flow path 6*c*, the second port 52, and the third port 53 and is stored into the reservoir in the suction-discharge unit 7. When, for example, the suction-discharge unit 7 includes the opening for sucking and discharging a liquid in its lower portion, air sucked from the flow paths by the suction-discharge unit 7 floats in the first liquid L1 in the reservoir in the suction-discharge unit 7.

During the first suction process, for example, the liquid feeder 4 continues feeding the second liquid L2 through the third connection flow path 4*c* and the first inlet opening 1*i* to the flow path portion 30 in the first flow path device 3. For example, after the second liquid L2 fills the flow path portion 30, the outlet hole 326, the outlet hole 328, and the outlet hole 329, the second liquid L2 may be fed in a decreased feed amount per unit time (feed rate) from the liquid feeder 4 through the first inlet opening 1*i* to the flow path portion 30.

Pressurizing Process

In the pressurizing process in step Sa4, the switcher 5 is set to the first state allowing a liquid flow between the first port 51 and the second port 52. In this state, a pressure is applied to the first liquid L1 in the suction-discharge unit 7.

Figure 9:
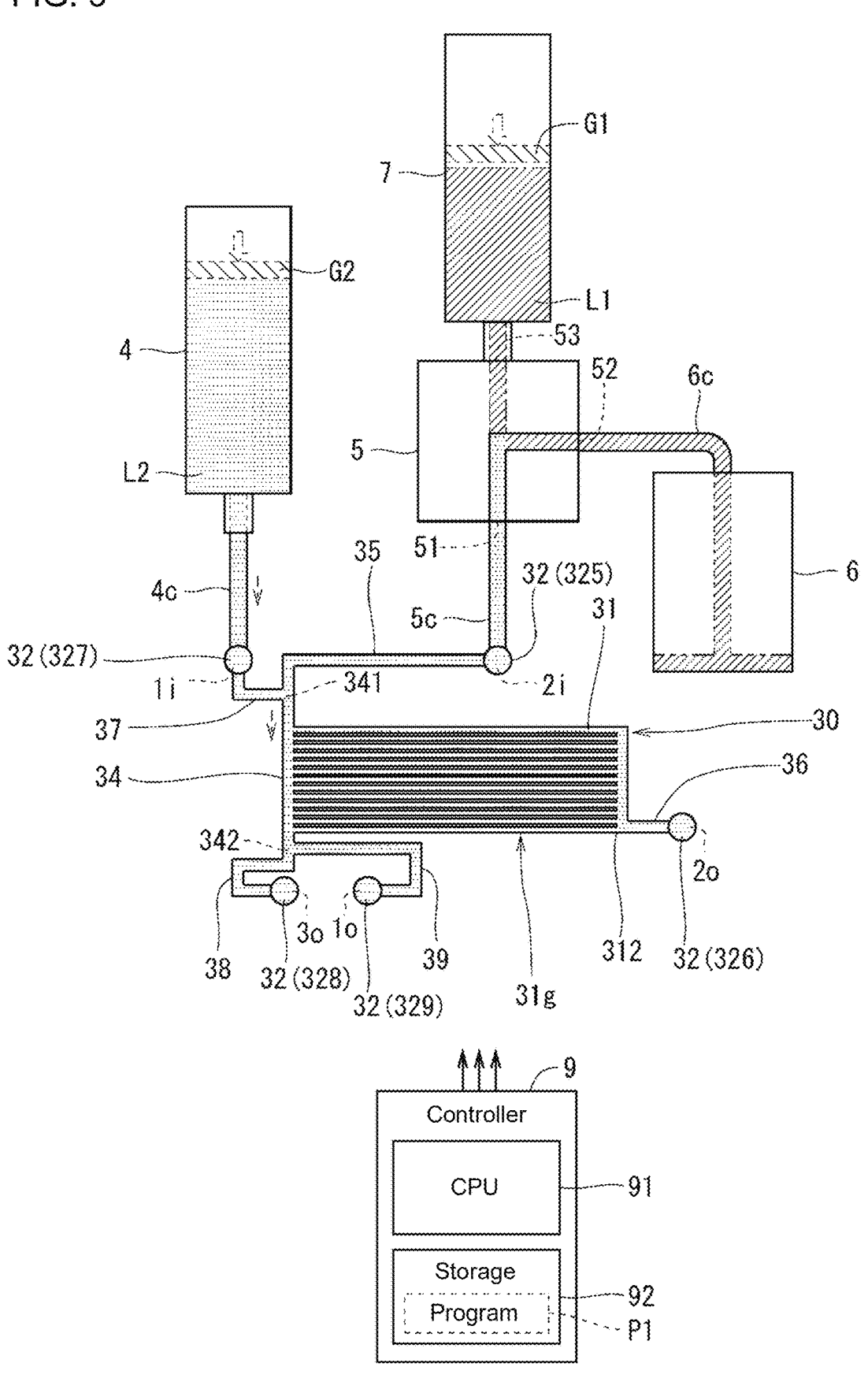
FIG. 9 is a conceptual diagram of the first flow path device and the components, illustrating their example states in a pressurizing process.

FIG. 9 is a conceptual diagram of the first flow path device 3 and the components, illustrating their example states in the pressurizing process. In FIG. 9, the two-dot-dash outlined arrow indicates the direction in which each of the first gasket G1 and the second gasket G2 is pushed.

In the pressurizing process, for example, a pressure is applied to air in the reservoir in the suction-discharge unit 7 to apply a pressure to the first liquid L1 in the reservoir in the suction-discharge unit 7. When, for example, the suction-discharge unit 7 is a syringe pump, the first gasket G1 is pushed down to apply a pressure to the first liquid L1 in the suction-discharge unit 7 through the air above the first liquid L1. This can smoothly start injection of the first liquid L1 into the flow path portion 30 in the first flow path device 3 from the suction-discharge unit 7 through, for example, the switcher 5 after the switcher 5 is set to the third state allowing a liquid flow between the first port 51 and the third port 53 in the introduction process in step Sa5.

The pressurizing process may be performed for a short period. When, for example, the second liquid L2 has filled the flow path portion 30, the outlet hole 326, the outlet hole 328, and the outlet hole 329 before the pressurizing process, the second liquid L2 is fed in a smaller feed amount per unit time (feed rate) from the liquid feeder 4 through the first inlet opening 1*i* to the flow path portion 30. Thus, during the period of the pressurizing process, a small amount of or substantially no second liquid L2 flows from the liquid feeder 4 through, for example, the first flow path device 3 and the switcher 5 toward the liquid storage 6. During the period of the pressurizing process, for example, the liquid feeder 4 may stop feeding the second liquid L2 through the first inlet opening 1*i* to the flow path portion 30. These various operations can reduce waste liquid resulting from, for example, wasteful discharge of the second liquid L2.

Introduction Process

In the introduction process in step Sa5, the switcher 5 is set to the third state allowing a liquid flow between the first port 51 and the third port 53. In this state, the suction-discharge unit 7 introduces the first liquid L1 into the flow path portion 30 through the third port 53, the first port 51, and the second inlet opening 2*i*.

Figure 10:
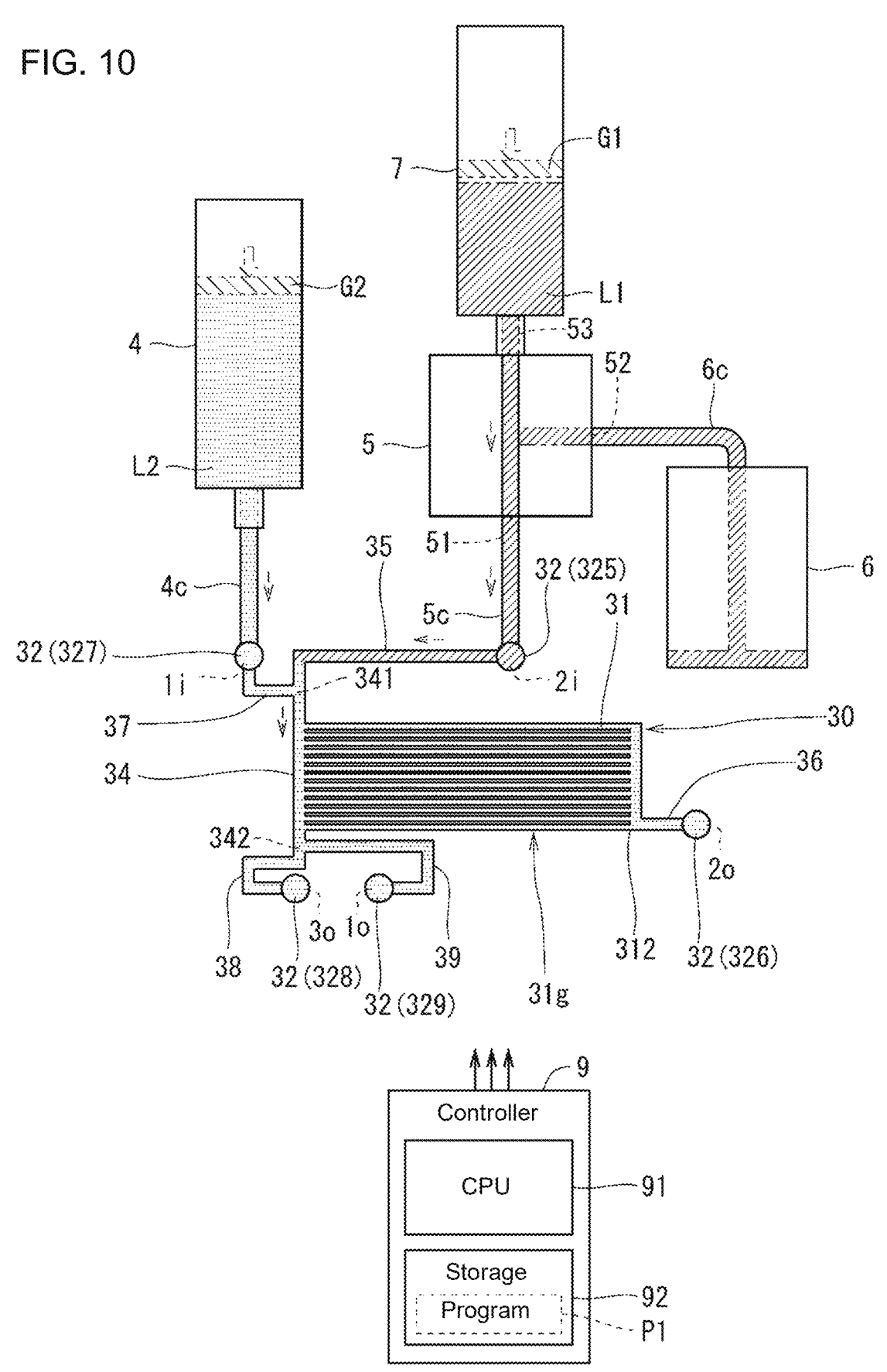
FIG. 10 is a conceptual diagram of the first flow path device and the components, illustrating their example states in an introduction process.

FIG. 10 is a conceptual diagram of the first flow path device 3 and the components, illustrating their example states in the introduction process. In FIG. 10, the two-dot-dash outlined arrow indicates the direction in which each of the first gasket G1 and the second gasket G2 is pushed.

In the introduction process, as illustrated in FIG. 10, the suction-discharge unit 7 injects the first liquid L1 into the flow path portion 30 through, for example, the switcher 5 and the second inlet opening 2*i*, and the liquid feeder 4 injects the second liquid L2 into the flow path portion 30 through, for example, the first inlet opening 1*i*. In the example in FIG. 10, the first liquid L1 stored in the suction-discharge unit 7 is discharged from the suction-discharge unit 7 and flows through the third port 53, the first port 51, and the inlet hole 325 into the flow path 35 in the flow path portion 30. The second liquid L2 discharged from the liquid feeder 4 flows through the third connection flow path 4*c*, the first inlet opening 1*i*, and the inlet hole 327 into the flow path 37 in the flow path portion 30. In this example, the first liquid L1 flows through the flow path 35 into the first upstream portion 341 in the main flow path 34, and the second liquid L2 flows through the flow path 37 into the first upstream portion 341 in the main flow path 34. The first flow path device 3 thus performs the process (particle separating process) of separating the separating target particles P100 from the non-target particles P200 in the first liquid L1 and discharging the separating target particles P100, as described above.

The filling process to the introduction process described above reduce waste liquid resulting from, for example, wasteful discharge of the first liquid L1. The reduced waste of the first liquid L1 allows, for example, efficient use of the first liquid L1 in various processes with the first flow path device 3.

In the first embodiment, for example, the pressurizing process described above may be eliminated.

1-4. Overview of First Embodiment

The method for introducing a liquid into the first flow path device 3 according to the first embodiment includes the preparation process, the filling process, the first suction process, and the introduction process that are performed in this order. In the preparation process, a connection is established between the first flow path device 3 and the switcher 5 to allow a liquid flow between the second inlet opening 2i in the first flow path device 3 and the first port 51 in the switcher 5. In the preparation process, a connection is established between the internal space of the liquid storage 6 and the second port 52 to allow a liquid flow between the internal space and the second port 52. In the preparation process, a connection is established between the suction-discharge unit 7 and the third port 53 to allow a liquid flow between the suction-discharge unit 7 and the third port 53. In the preparation process, a connection is established between the liquid feeder 4 and the first inlet opening 1i to allow a liquid flow between the liquid feeder 4 and the first inlet opening 1i. The switcher 5 may be selectively set to one of the first state allowing a liquid flow between the first port 51 and the second port 52, the second state allowing a liquid flow between the second port 52 and the third port 53, and the third state allowing a liquid flow between the first port 51 and the third port 53. In the filling process, the switcher 5 is set to the first state, and the liquid feeder 4 feeds the second liquid L2 to fill, with the second liquid L2, the flow path from the liquid feeder 4 through the first inlet opening 1i, the flow path portion 30, the second inlet opening 2i, the first port 51, and the second port 52 to the liquid storage 6. In the first suction process, the switcher 5 is set to the second state, and the suction-discharge unit 7 sucks the first liquid L1 from the liquid storage 6 through the second port 52 and the third port 53 into the suction-discharge unit 7. In the introduction process, the switcher 5 is set to the third state, and the suction-discharge unit 7 introduces the first liquid L1 into the flow path portion 30 through the third port 53, the first port 51, and the second inlet opening 2i.

These operations reduce waste liquid resulting from wasteful discharge of the first liquid L1 and the second liquid L2 when the first liquid L1 is introduced into the first flow path device 3 after the second liquid L2 is fed to fill the flow path portion 30 in the first flow path device 3. Thus, the first liquid L1 as a process target can be introduced into the first flow path device 3 with less waste liquid.

When the first liquid L1 is blood and the second liquid L2 is saline, for example, the blood as a process target can be introduced into the first flow path device 3 with less waste of saline and blood, which is a precious sample.

2. OTHER EMBODIMENTS

The present disclosure is not limited to the first embodiment described above and may be changed or varied in various manners without departing from the spirit and scope of the present disclosure.

2-1. Second Embodiment

In the first embodiment, the method for introducing a liquid into the first flow path device 3 may further include, for example, a mixing process between the first suction process and the introduction process. When the method for introducing a liquid into the first flow path device 3 includes a pressurizing process, the method may further include the mixing process between the first suction process and the pressurizing process. In the mixing process, the switcher 5 is set to the third state, and the suction-discharge unit 7 sucks the second liquid L2 through the first port 51 and the third port 53 into the suction-discharge unit 7. The second liquid L2 is thus mixed with the first liquid L1 that has been sucked and stored in the reservoir in the suction-discharge unit 7. This mixing process may produce, for example, a liquid mixture L1a that is a mixture of the first liquid L1 and the second liquid L2. In this case, in the introduction process, the suction-discharge unit 7 introduces the first liquid L1 mixed with the second liquid L2 (also referred to as the liquid mixture L1a) produced in the mixing process into the flow path portion 30 through the third port 53, the first port 51, and the second inlet opening 2i.

This structure eliminates the process of, for example, preliminarily mixing the second liquid L2 with the first liquid L1 to reduce the concentration of the first liquid L1. This facilitates, for example, the introduction of the first liquid L1 as a process target into the first flow path device 3, with the concentration of the first liquid L1 lowered. When the first liquid L1 is blood and the second liquid L2 is saline, for example, the structure facilitates the introduction of blood into the first flow path device 3, with the blood diluted with saline.

Figure 11:
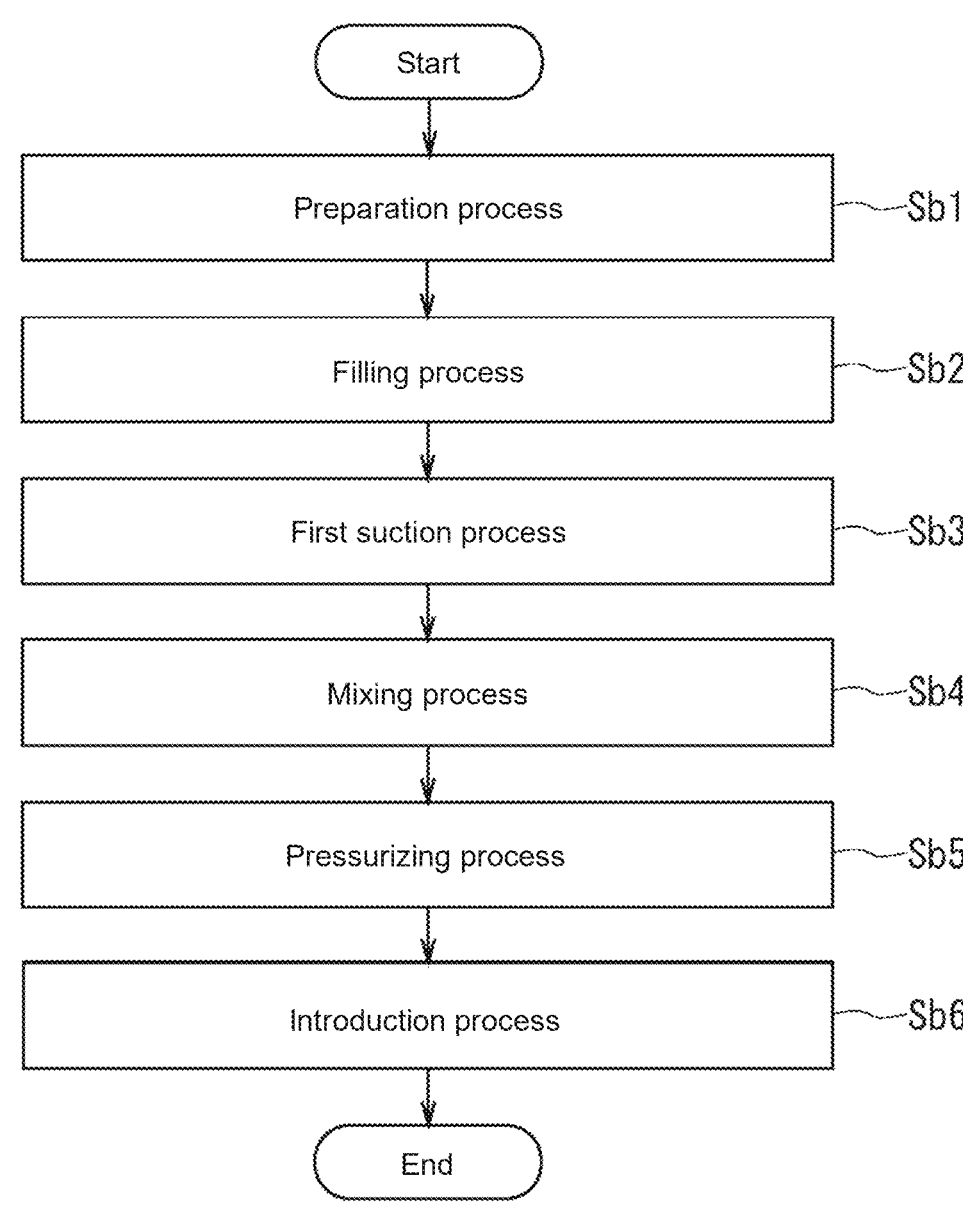
FIG. 11 is a flowchart of example processing with a method for introducing a liquid into the first flow path device according to a second embodiment.

FIG. 11 is a flowchart of example processing with a method for introducing a liquid into the first flow path device 3 according to a second embodiment.

In this example, as illustrated in FIG. 11, the preparation process in step Sb1, the filling process in step Sb2, the first suction process in step Sb3, the mixing process in step Sb4, the pressurizing process in step Sb5, and the introduction process in step Sb6 are performed in this order. In other words, the method for introducing a liquid into the first flow path device 3 includes the preparation process, the filling process, the first suction process, the mixing process, the pressurizing process, and the introduction process.

Figure 12:
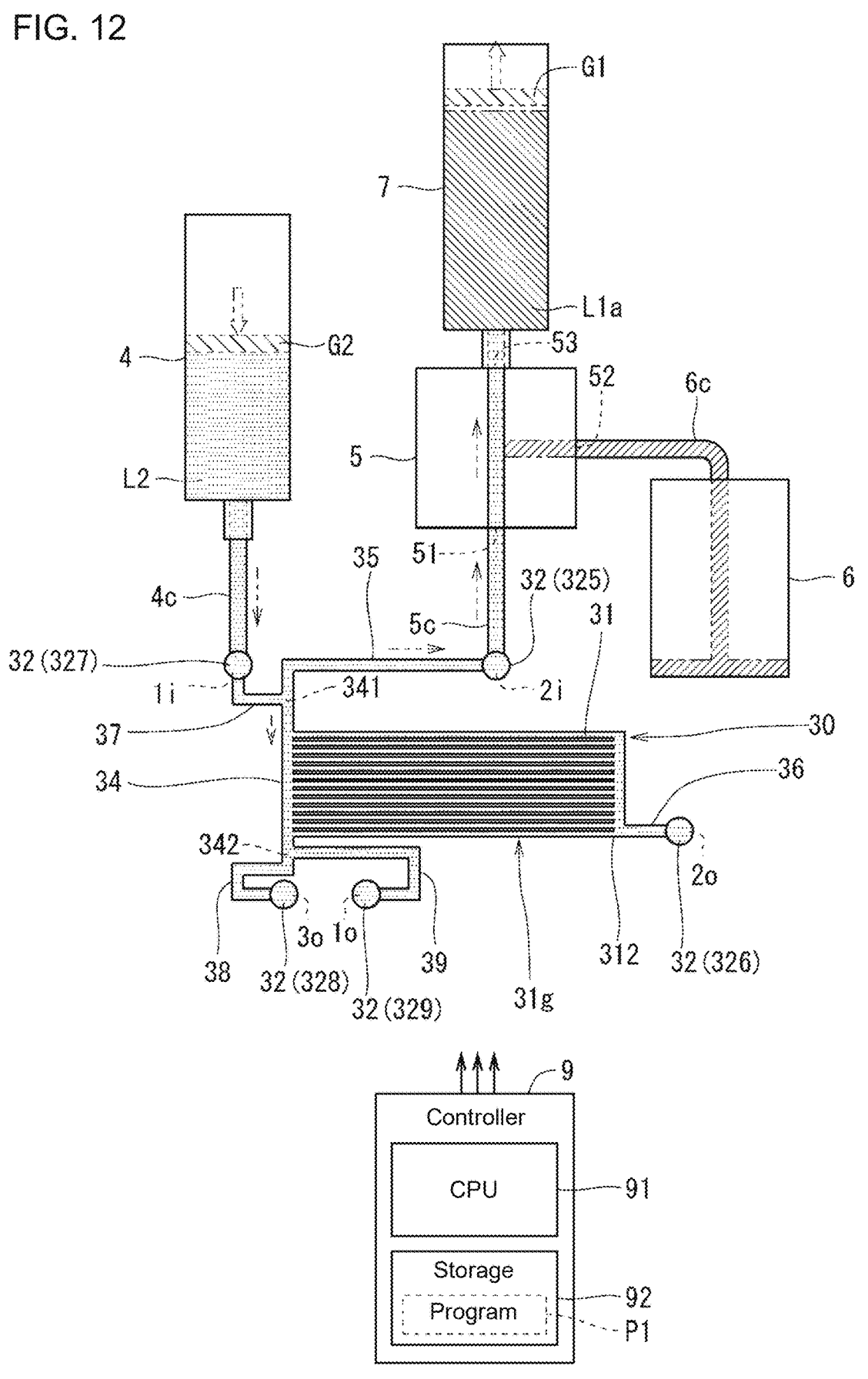
Figure 13:
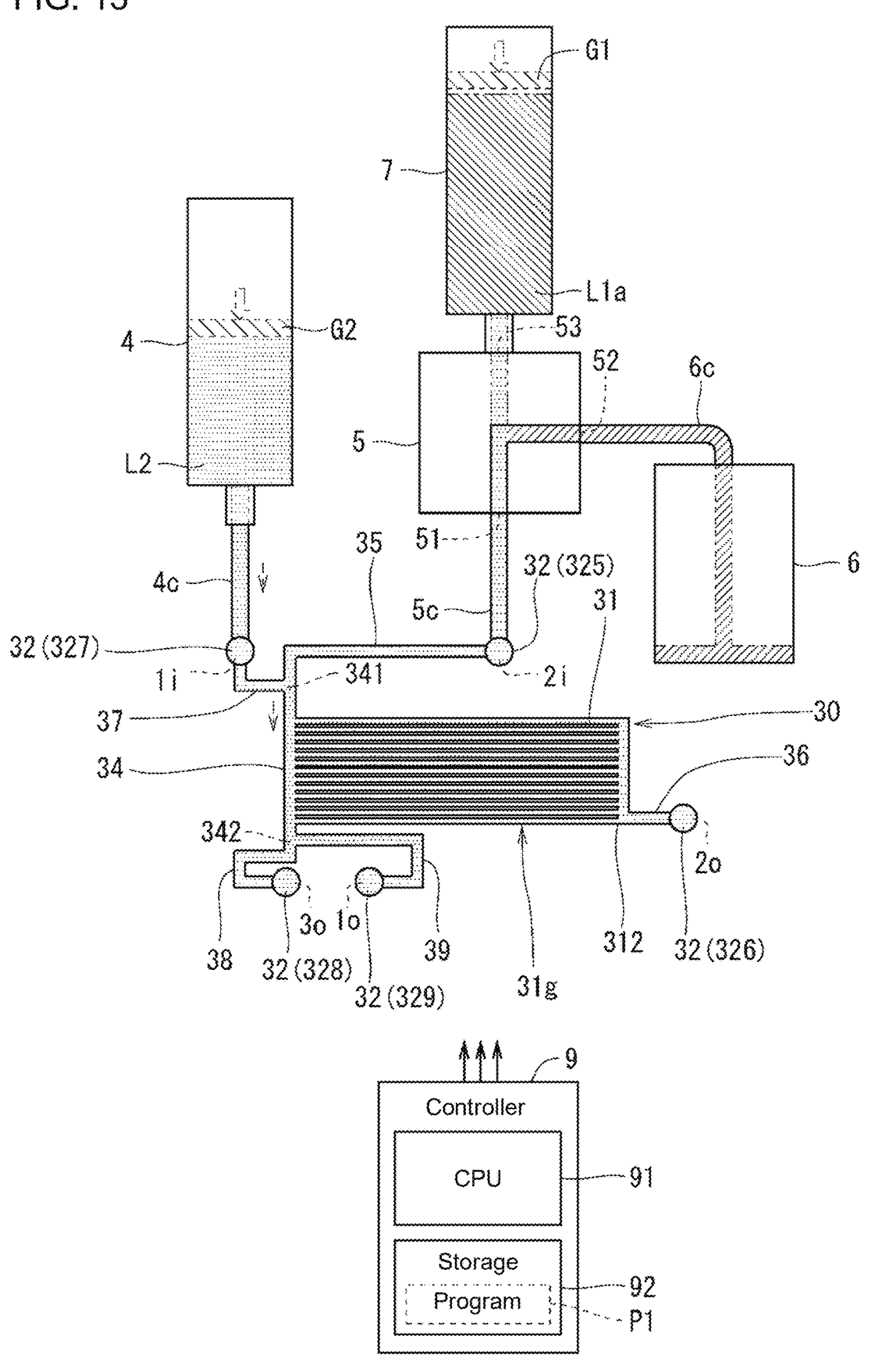
FIG. 13 is a conceptual diagram of the first flow path device and the components, illustrating their example states in a pressurizing process.
Figure 14:
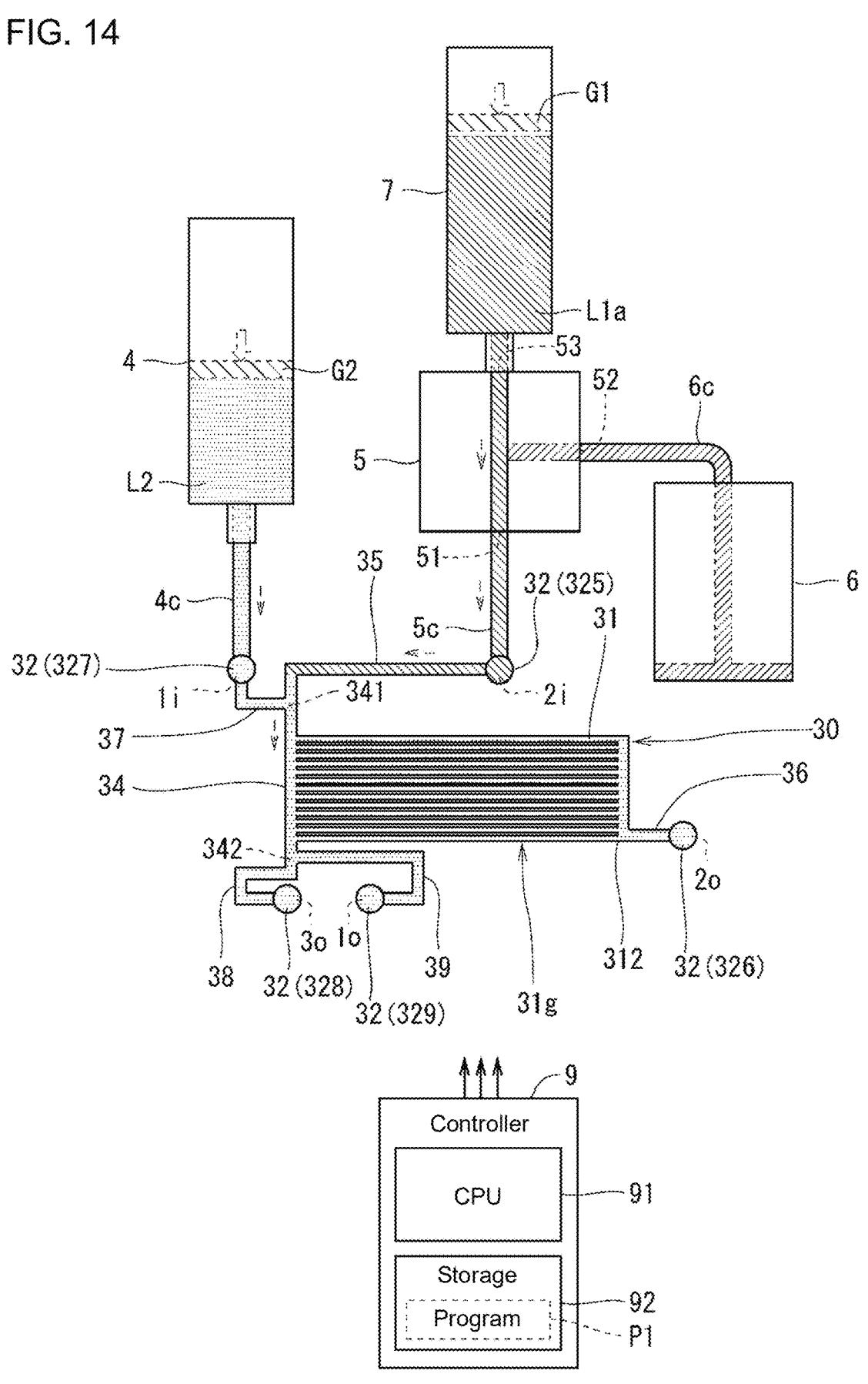
FIG. 14 is a conceptual diagram of the first flow path device and the components, illustrating their example states in an introduction process.

FIGS. 12 to 14 are each a conceptual diagram of the first flow path device 3 and the components, illustrating their example states in the corresponding process. The components include the switcher 5, the liquid storage 6, the suction-discharge unit 7, and the liquid feeder 4. In FIGS. 12 to 14, the area with the first liquid L1 is hatched with diagonal lines from the lower left to the upper right, the area with the second liquid L2 is hatched with a dot pattern, and the area with the liquid mixture L1a is hatched with closely spaced diagonal lines from the lower right to the upper left. In FIGS. 12 to 14, as in FIGS. 6 to 10 above, the upper surface of the liquid is schematically drawn with thin two-dot-dash lines, and the direction in which the liquid flows is schematically drawn with thin two-dot-dash arrows. In the examples in FIGS. 12 to 14, as in the examples in FIGS. 6 to 10 above, each of the suction-discharge unit 7 and the liquid feeder 4 is a syringe pump. The area with the first gasket G1 in the suction-discharge unit 7 and the area with the second gasket G2 in the liquid feeder 4 are each hatched with widely spaced diagonal lines from the lower right to the upper left. The outer edge of each of the first gasket G1 and the second gasket G2 is schematically indicated by dashed lines. A component such as a plunger for pushing and pulling each of the first gasket G1 and the second gasket G2 is not illustrated. To facilitate understanding of the connection states and the operation states of the components, FIGS. 12 to 14 illustrate the components such as the switcher 5, the liquid storage 6, the suction-discharge unit 7, and the liquid feeder 4 with their vertical direction aligned with the vertical direction in the figures (the upward direction in the figures is the positive Z-direction, and the downward direction in the figures is the negative Z-direction), and illustrate the multiple flow paths and the multiple holes in the first flow path device 3 with their upward direction (positive Z-direction) aligned with the frontward direction in the figures for convenience, as in FIGS. 6 to 10 above.

In the preparation process in step Sb1, for example, the same operation is performed as in the preparation process in step Sa1 in the first embodiment.

In the filling process in step Sb2, for example, the same operation is performed as in the filling process in step Sa2 in the first embodiment. This can reduce waste liquid resulting from, for example, wasteful discharge of the second liquid L2. In the second embodiment, when a large amount of the second liquid L2 is mixed with the first liquid L1 in the mixing process, a certain amount of the second liquid L2 may be mixed with the first liquid L1 in the liquid storage 6 in the filling process.

In the first suction process in step Sb3, for example, the same operation is performed as in the first suction process in step Sa3 in the first embodiment.

In the mixing process in step Sb4, the switcher 5 is set to the third state allowing a liquid flow between the first port 51 and the third port 53. In this state, the suction-discharge unit 7 sucks the second liquid L2 through the first port 51 and the third port 53 into the suction-discharge unit 7. The second liquid L2 is thus mixed with the first liquid L1 that has been sucked and stored in the reservoir in the suction-discharge unit 7. This may produce, for example, the liquid mixture L1a that is a mixture of the first liquid L1 and the second liquid L2.

FIG. 12 is a conceptual diagram of the first flow path device 3 and the components, illustrating their example states in the mixing process. In FIG. 12, the two-dot-dash outlined arrow indicates each of the direction in which the first gasket G1 is pulled and the direction in which the second gasket G2 is pushed.

In the mixing process, as illustrated in FIG. 12, the suction-discharge unit 7 sucks the second liquid L2 from the flow path portion 30 in the first flow path device 3. For example, the suction-discharge unit 7 sucks the second liquid L2 from the flow path portion 30 through the inlet hole 325, the first port 51, and the third port 53 while the liquid feeder 4 is feeding the second liquid L2 to the flow path portion 30 in the first flow path device 3 through the first inlet opening 1i. The second liquid L2 is thus mixed with the first liquid L1 stored in the reservoir in the suction-discharge unit 7 to produce the liquid mixture L1a as a mixture of the first liquid L1 and the second liquid L2. When the first liquid L1 is blood and the second liquid L2 is saline, for example, the liquid mixture L1a is a liquid resulting from diluting blood as the first liquid L1 or a process target with saline as the second liquid L2. In this example, the liquid mixture L1a is stored into the reservoir in the suction-discharge unit 7. In this mixing process, for example, the suction amount per unit time (the suction rate) of the second liquid L2 sucked by the suction-discharge unit 7 is set to a value less than or equal to the feed amount per unit time (the feed rate) of the second liquid L2 fed from the liquid feeder 4.

In the pressurizing process in step Sb5, the switcher 5 is set to the first state allowing a liquid flow between the first port 51 and the second port 52. In this state, a pressure is applied to the liquid mixture L1a in the reservoir in the suction-discharge unit 7.

FIG. 13 is a conceptual diagram of the first flow path device 3 and the components, illustrating their example states in the pressurizing process. In FIG. 13, as in FIG. 9 above, the two-dot-dash outlined arrow indicates the direction in which each of the first gasket G1 and the second gasket G2 is pushed.

In the pressurizing process, for example, a pressure is applied to air in the reservoir in the suction-discharge unit 7 to apply a pressure to the liquid mixture L1a in the reservoir in the suction-discharge unit 7. When, for example, the suction-discharge unit 7 is a syringe pump, the first gasket G1 is pushed down to apply a pressure to the liquid mixture L1a in the suction-discharge unit 7 through the air above the liquid mixture L1a. This can smoothly start injection of the liquid mixture L1a into the flow path portion 30 in the first flow path device 3 from the suction-discharge unit 7 through, for example, the switcher 5 after the switcher 5 is set to the third state allowing a liquid flow between the first port 51 and the third port 53 in the introduction process in step Sb6.

The pressurizing process may be performed for a short period. When, for example, the second liquid L2 has filled the flow path portion 30, the outlet hole 326, the outlet hole 328, and the outlet hole 329 before the pressurizing process, the second liquid L2 is fed in a smaller feed amount per unit time (feed rate) from the liquid feeder 4 through the first inlet opening 1i to the flow path portion 30. Thus, during the period of the pressurizing process, a small amount of or substantially no second liquid L2 flows from the liquid feeder 4 through, for example, the first flow path device 3 and the switcher 5 toward the liquid storage 6. During the period of the pressurizing process, for example, the liquid feeder 4 may stop feeding the second liquid L2 through the first inlet opening 1i to the flow path portion 30. These various operations can reduce waste liquid resulting from, for example, wasteful discharge of the second liquid L2.

In the introduction process in step Sb6, the suction-discharge unit 7 introduces the first liquid L1 mixed with the second liquid L2 (liquid mixture L1a) produced in the mixing process into the flow path portion 30 through the third port 53, the first port 51, and the second inlet opening 2i.

FIG. 14 is a conceptual diagram of the first flow path device 3 and the components, illustrating their example states in the introduction process. In FIG. 14, as in FIG. 10 above, the two-dot-dash outlined arrow indicates the direction in which each of the first gasket G1 and the second gasket G2 is pushed.

In the introduction process, as illustrated in FIG. 14, the suction-discharge unit 7 injects the liquid mixture L1a into the flow path portion 30 through, for example, the switcher 5 and the second inlet opening 2i, and the liquid feeder 4 injects the second liquid L2 into the flow path portion 30 through, for example, the first inlet opening 1i. In the example in FIG. 14, the liquid mixture L1a stored in the suction-discharge unit 7 is discharged from the suction-discharge unit 7 and flows through the third port 53, the first port 51, and the inlet hole 325 into the flow path 35 in the flow path portion 30. The second liquid L2 discharged from the liquid feeder 4 flows through the third connection flow path 4c, the first inlet opening 1i, and the inlet hole 327 into the flow path 37 in the flow path portion 30. In this example, the liquid mixture L1a flows through the flow path 35 into the first upstream portion 341 in the main flow path 34, and the second liquid L2 flows through the flow path 37 into the first upstream portion 341 in the main flow path 34. The first flow path device 3 thus performs the process (particle separating process) of separating the separating target particles P100 from the non-target particles P200 in the liquid mixture L1*a* and discharging the separating target particles P100.

The filling process to the introduction process in the second embodiment also reduce waste liquid resulting from, for example, wasteful discharge of the first liquid L1 and the liquid mixture L1*a*. The reduced waste of the first liquid L1 allows, for example, efficient use of the first liquid L1 in various processes with the first flow path device 3.

In the second embodiment as well, for example, the pressurizing process described above may be eliminated.

2-2. Third Embodiment

In the first embodiment, the method for introducing a liquid into the first flow path device 3 may further include, for example, a second suction process between the filling process and the first suction process. In the second suction process, the switcher 5 is set to the third state, and the suction-discharge unit 7 sucks the second liquid L2 through the first port 51 and the third port 53 into the suction-discharge unit 7. In this case, in the first suction process, the suction-discharge unit 7 sucks the first liquid L1 from the liquid storage 6 through the second port 52 and the third port 53. The first liquid L1 is thus mixed with the second liquid L2 that has been sucked and stored in the reservoir in the suction-discharge unit 7. This process may produce, for example, the liquid mixture L1*a* that is a mixture of the first liquid L1 and the second liquid L2. In the introduction process, the suction-discharge unit 7 introduces the first liquid L1 mixed with the second liquid L2 (liquid mixture L1*a*) produced in the first suction process into the flow path portion 30 through the third port 53, the first port 51, and the second inlet opening 2*i*.

This structure eliminates the process of, for example, preliminarily mixing the second liquid L2 with the first liquid L1 to reduce the concentration of the first liquid L1. This facilitates, for example, the introduction of the first liquid L1 as a process target into the first flow path device 3, with the concentration of the first liquid L1 lowered. When the first liquid L1 is blood and the second liquid L2 is saline, for example, the structure facilitates the introduction of blood into the first flow path device 3, with the blood diluted with saline.

Figure 15:
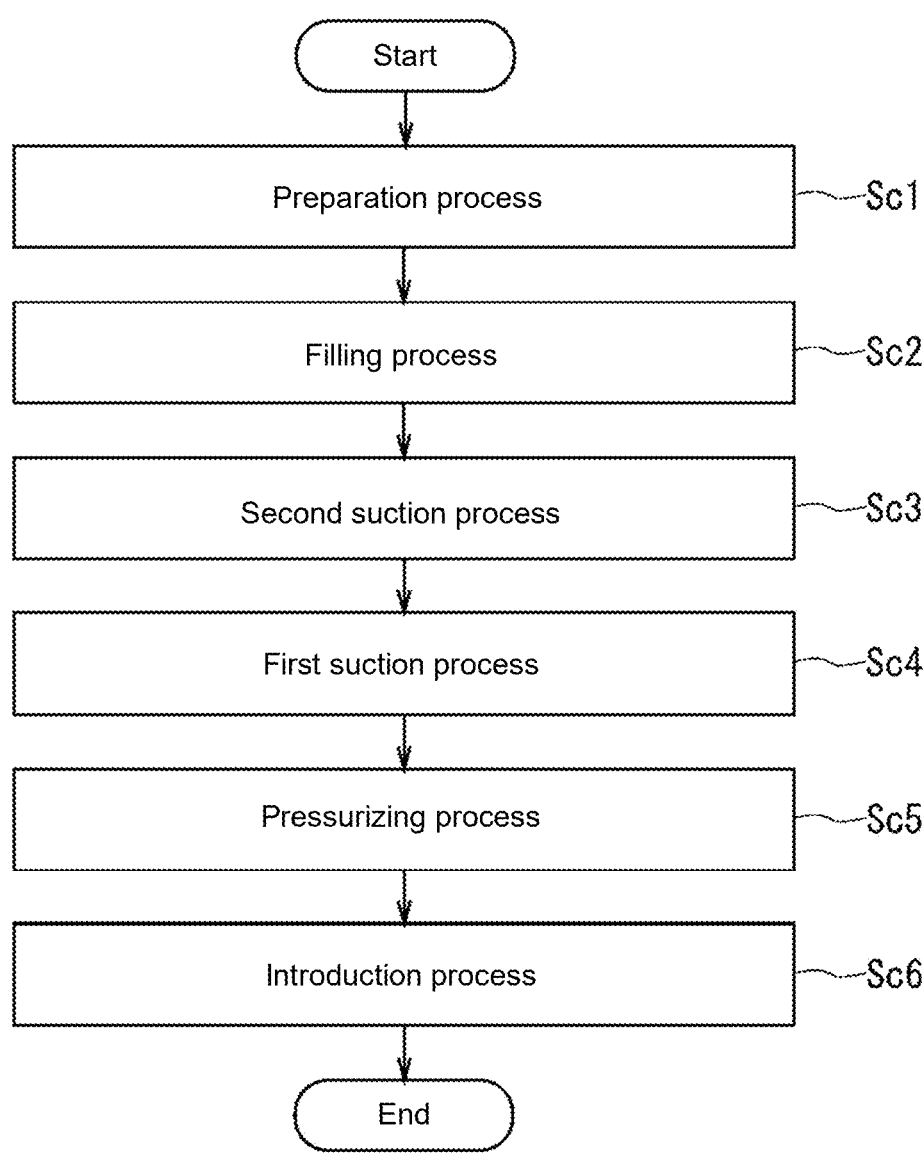
FIG. 15 is a flowchart of example processing with a method for introducing a liquid into the first flow path device according to a third embodiment.

FIG. 15 is a flowchart of example processing with a method for introducing a liquid into the first flow path device 3 according to a third embodiment.

In this example, as illustrated in FIG. 15, the preparation process in step Sc1, the filling process in step Sc2, the second suction process in step Sc3, the first suction process in step Sc4, the pressurizing process in step Sc5, and the introduction process in step Sc6 are performed in this order. In other words, the method for introducing a liquid into the first flow path device 3 includes the preparation process, the filling process, the second suction process, the first suction process, the pressurizing process, and the introduction process.

Figure 16:
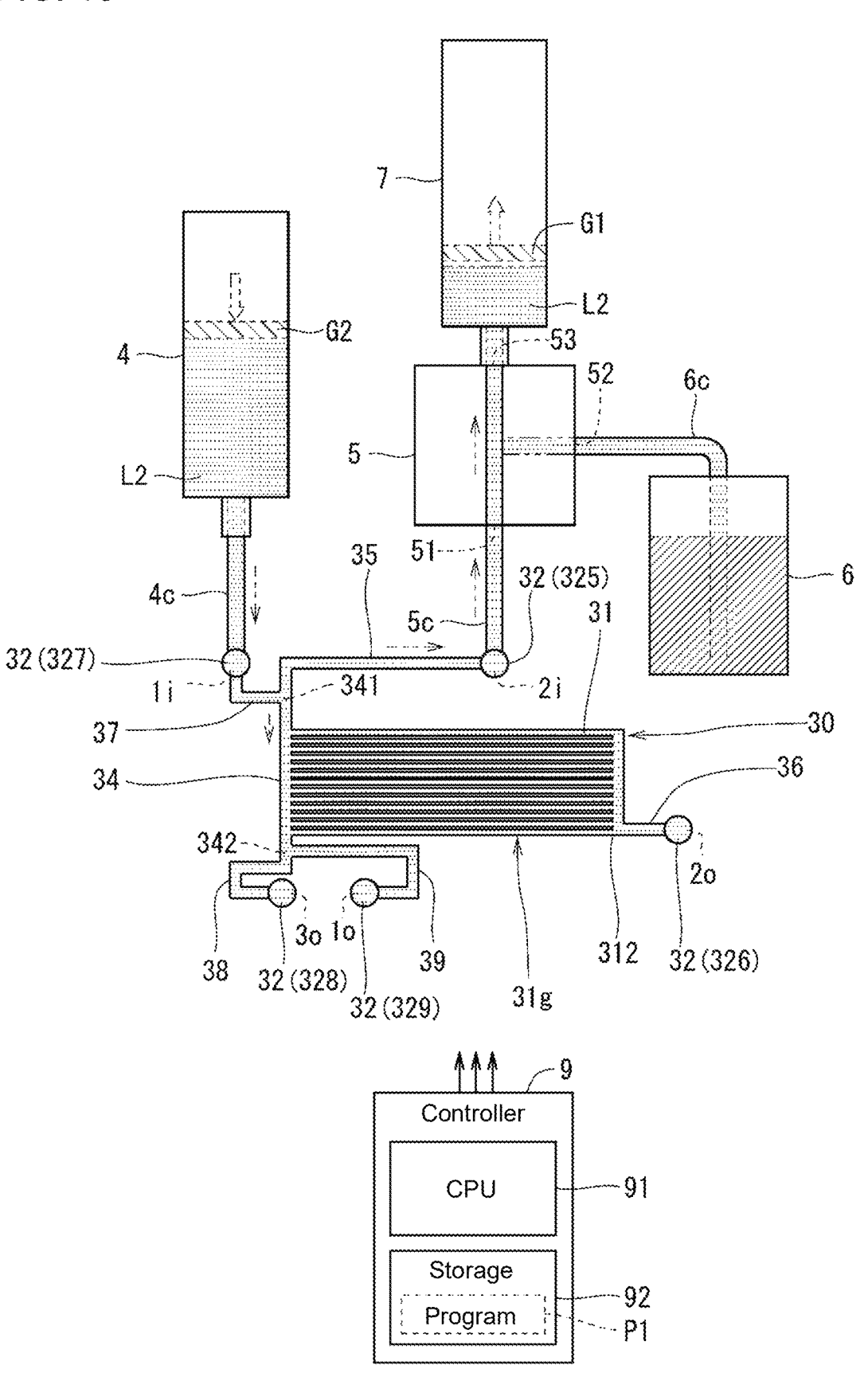
FIG. 16 is a conceptual diagram of the first flow path device and the components, illustrating their example states in a second suction process.
Figure 17:
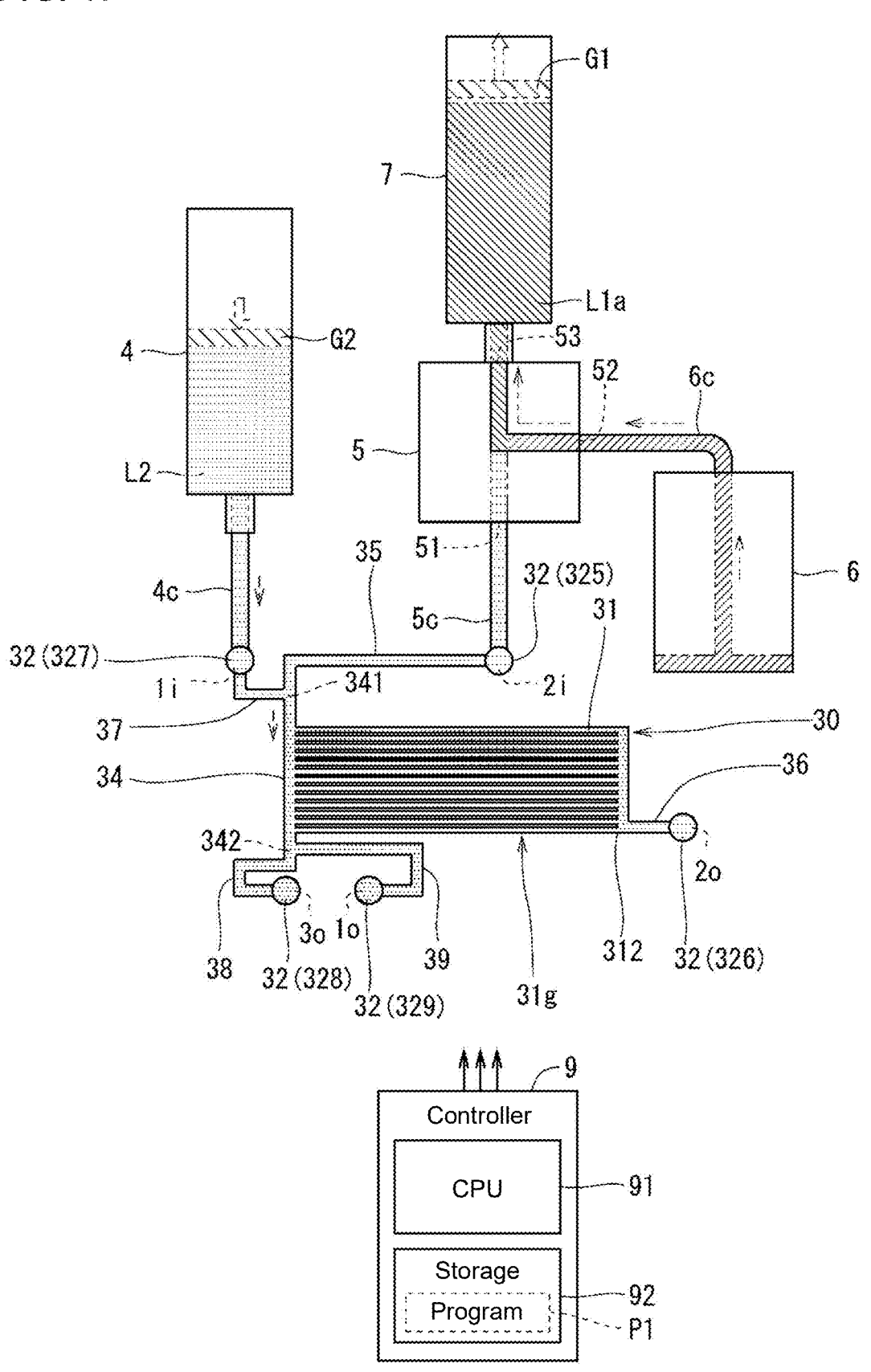
FIG. 17 is a conceptual diagram of the first flow path device and the components, illustrating their example states in a first suction process.

FIGS. 16 and 17 are each a conceptual diagram of the first flow path device 3 and the components, illustrating their example states in the corresponding process. The components include the switcher 5, the liquid storage 6, the suction-discharge unit 7, and the liquid feeder 4. In FIGS. 16 and 17, as in FIGS. 12 to 14 above, the area with the first liquid L1 is hatched with diagonal lines from the lower left to the upper right, the area with the second liquid L2 is hatched with a dot pattern, and the area with the liquid mixture L1*a* is hatched with closely spaced diagonal lines from the lower right to the upper left. In FIGS. 16 and 17, as in FIGS. 6 to 10 and 12 to 14 above, the upper surface of the liquid is schematically drawn with thin two-dot-dash lines, and the direction in which the liquid flows is schematically drawn with thin two-dot-dash arrows. In the examples in FIGS. 16 and 17, as in the examples in FIGS. 6 to 10 and 12 to 14 above, each of the suction-discharge unit 7 and the liquid feeder 4 is a syringe pump. The area with the first gasket G1 in the suction-discharge unit 7 and the area with the second gasket G2 in the liquid feeder 4 are each hatched with widely spaced diagonal lines from the lower right to the upper left. The outer edge of each of the first gasket G1 and the second gasket G2 is schematically indicated by dashed lines. A component such as a plunger for pushing and pulling each of the first gasket G1 and the second gasket G2 is not illustrated. To facilitate understanding of the connection states and the operation states of the components, FIGS. 16 and 17 illustrate the components such as the switcher 5, the liquid storage 6, the suction-discharge unit 7, and the liquid feeder 4 with their vertical direction aligned with the vertical direction in the figures (the upward direction in the figures is the positive Z-direction, and the downward direction in the figures is the negative Z-direction), and illustrate the multiple flow paths and the multiple holes in the first flow path device 3 with their upward direction (positive Z-direction) aligned with the frontward direction in the figures for convenience, as in FIGS. 6 to 10 and 12 to 14 above.

In the preparation process in step Sc1, for example, the same operation is performed as in the preparation process in step Sa1 in the first embodiment.

In the filling process in step Sc2, for example, the same operation is performed as in the filling process in step Sa2 in the first embodiment. This can reduce waste liquid resulting from, for example, wasteful discharge of the second liquid L2. In the third embodiment, when a large amount of the second liquid L2 is mixed with the first liquid L1 in the first suction process, a certain amount of the second liquid L2 may be mixed with the first liquid L1 in the liquid storage 6 in the filling process.

In the second suction process in step Sc3, the switcher 5 is set to the third state allowing a liquid flow between the first port 51 and the third port 53. In this state, the suction-discharge unit 7 sucks the second liquid L2 through the first port 51 and the third port 53 into the suction-discharge unit 7. The second liquid L2 is thus stored into the reservoir in the suction-discharge unit 7.

FIG. 16 is a conceptual diagram of the first flow path device 3 and the components, illustrating their example states in the second suction process. In FIG. 16, the two-dot-dash outlined arrow indicates each of the direction in which the first gasket G1 is pulled and the direction in which the second gasket G2 is pushed.

In the second suction process, as illustrated in FIG. 16, the suction-discharge unit 7 sucks the second liquid L2 from the flow path portion 30 in the first flow path device 3. For example, the suction-discharge unit 7 sucks the second liquid L2 from the flow path portion 30 through the inlet hole 325, the first port 51, and the third port 53 while the liquid feeder 4 is feeding the second liquid L2 to the flow path portion 30 in the first flow path device 3 through the first inlet opening 1*i*. The second liquid L2 is thus stored into the reservoir in the suction-discharge unit 7. When, for example, the suction-discharge unit 7 includes the opening for sucking and discharging a liquid in its lower portion, air sucked from the flow paths by the suction-discharge unit 7 floats in the second liquid L2 in the reservoir in the suction-discharge unit 7. In this second suction process, for example, the suction amount per unit time (the suction rate) of the second liquid L2 sucked by the suction-discharge unit 7 is set to a value less than or equal to the feed amount per unit time (the feed rate) of the second liquid L2 fed from the liquid feeder 4.

In the first suction process in step Sc4, the switcher 5 is set to the second state allowing a liquid flow between the second port 52 and the third port 53. In this state, the suction-discharge unit 7 sucks the first liquid L1 from the liquid storage 6 through the second port 52 and the third port 53 into the suction-discharge unit 7. The first liquid L1 is thus mixed with the second liquid L2 that has been sucked and stored in the reservoir in the suction-discharge unit 7. This may produce, for example, the liquid mixture L1a that is a mixture of the first liquid L1 and the second liquid L2.

FIG. 17 is a conceptual diagram of the first flow path device 3 and the components, illustrating their example states in the first suction process. In FIG. 17, the two-dot-dash outlined arrow indicates each of the direction in which the first gasket G1 is pulled and the direction in which the second gasket G2 is pushed.

In the first suction process, as illustrated in FIG. 17, the suction-discharge unit 7 sucks the first liquid L1 from the liquid storage 6. For example, the suction-discharge unit 7 sucks the first liquid L1 stored in the liquid storage 6 through the second connection flow path 6c, the second port 52, and the third port 53 into the suction-discharge unit 7. The first liquid L1 is thus mixed with the second liquid L2 stored in the reservoir in the suction-discharge unit 7 to produce the liquid mixture L1a as a mixture of the first liquid L1 and the second liquid L2. When the first liquid L1 is blood and the second liquid L2 is saline, for example, the liquid mixture L1a is a liquid resulting from diluting blood as the first liquid L1 or a process target with saline as the second liquid L2. In this example, the liquid mixture L1a is stored into the reservoir in the suction-discharge unit 7. When, for example, the suction-discharge unit 7 includes the opening for sucking and discharging a liquid in its lower portion, air sucked from the flow paths by the suction-discharge unit 7 floats in the liquid mixture L1a in the reservoir in the suction-discharge unit 7.

During the first suction process, for example, the liquid feeder 4 continues feeding the second liquid L2 through the third connection flow path 4c and the first inlet opening 1i to the flow path portion 30 in the first flow path device 3. For example, after the second liquid L2 fills the flow path portion 30, the outlet hole 326, the outlet hole 328, and the outlet hole 329, the second liquid L2 may be fed in a decreased feed amount per unit time (feed rate) from the liquid feeder 4 through the first inlet opening 1i to the flow path portion 30.

In the pressurizing process in step Sc5, for example, the same operation is performed as in the pressurizing process in step Sb5 in the second embodiment.

In the introduction process in step Sc6, for example, the same operation is performed as in the introduction process in step Sb6 in the second embodiment. For example, as illustrated in FIG. 14, the suction-discharge unit 7 introduces the first liquid L1 mixed with the second liquid L2 (liquid mixture L1a) produced in the first suction process into the flow path portion 30 through the third port 53, the first port 51, and the second inlet opening 2i. The first flow path device 3 thus performs the process (particle separating process) of separating the separating target particles P100 from the non-target particles P200 in the liquid mixture L1a and discharging the separating target particles P100.

The filling process to the introduction process in the third embodiment also reduce waste liquid resulting from, for example, wasteful discharge of the first liquid L1 and the liquid mixture L1a. The reduced waste of the first liquid L1 allows, for example, efficient use of the first liquid L1 in various processes with the first flow path device 3.

In the third embodiment as well, for example, the pressurizing process described above may be eliminated.

3. VARIATIONS

3-1. First Variation

The first flow path device 3 according to each of the above embodiments as a separating flow path device may be, for example, combined with a flow path device (also referred to as a second flow path device) 1 as a processing device to be included in a separating processing device 100 as a type of flow path device.

Example Schematic Structure of Separating Processing Device

Figure 18:
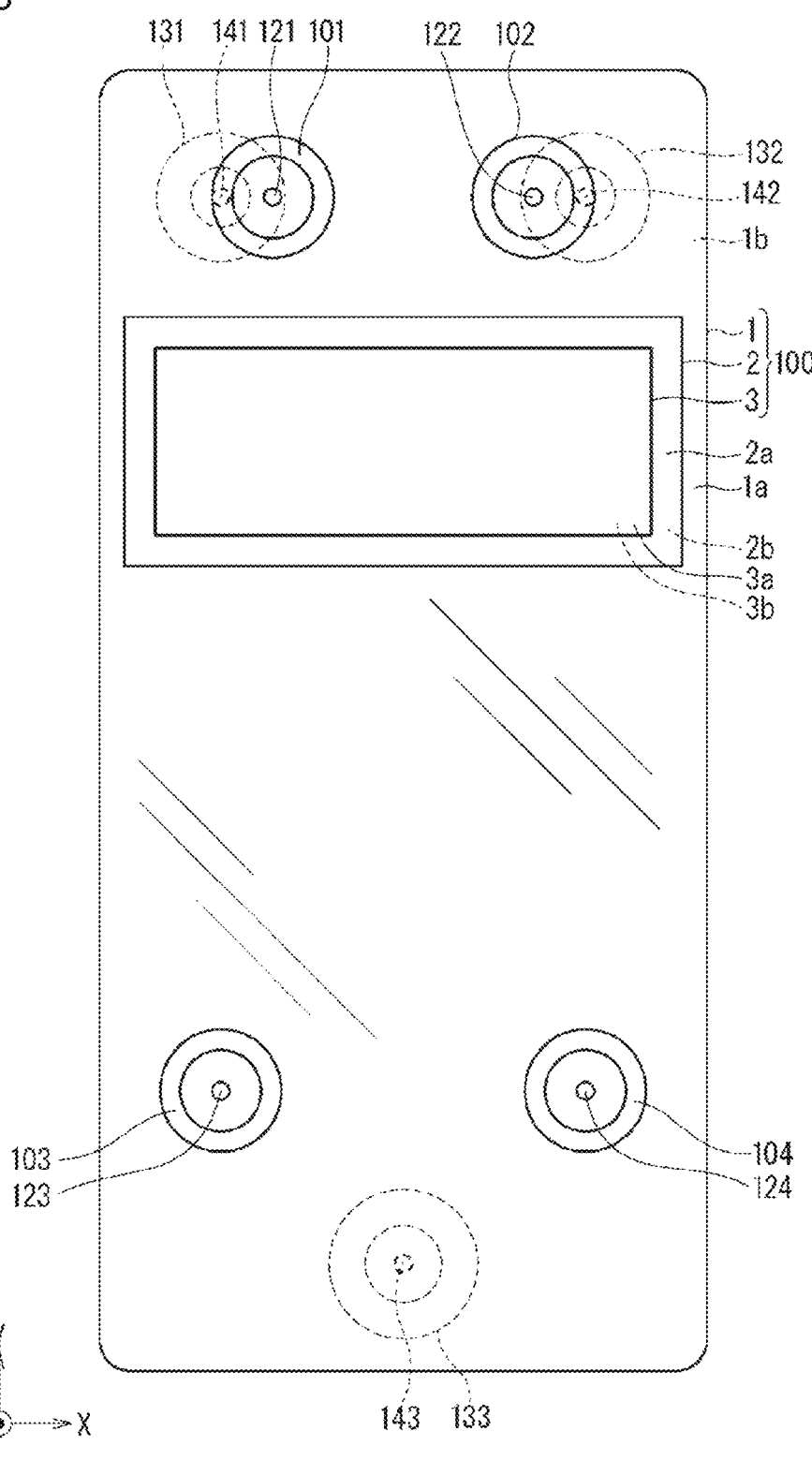
FIG. 18 is a schematic plan view of an example separating processing device according to a first variation.

FIG. 18 is a plan view of an example of the separating processing device 100 according to a first variation.

The separating processing device 100 includes, for example, the first flow path device 3, a connection member 2, and a second flow path device 1. The second flow path device 1, the connection member 2, and the first flow path device 3 are stacked on one another in the stated order in the positive Z-direction. In other words, the connection member 2 is located on the second flow path device 1, and the first flow path device 3 is located on the connection member 2.

The second flow path device 1 includes a surface (also referred to as a second upper surface) 1a and a surface (also referred to as a second lower surface) 1b. The second upper surface 1a is located in the positive Z-direction from the second lower surface 1b.

The connection member 2 includes a surface (also referred to as a third upper surface) 2a and a surface (also referred to as a third lower surface) 2b. The third upper surface 2a is located in the positive Z-direction from the third lower surface 2b. The third lower surface 2b is in contact with the second upper surface 1a of the second flow path device 1. The third upper surface 2a is in contact with the first lower surface 3b of the first flow path device 3. In other words, the connection member 2 is between the first lower surface 3b of the first flow path device 3 and the second upper surface 1a of the second flow path device 1. The third lower surface 2b is bonded to the second upper surface 1a by, for example, plasma bonding or optical bonding. The first lower surface 3b is bonded to the third upper surface 2a by, for example, plasma bonding or optical bonding. For the plasma bonding described above, for example, oxygen plasma is used. For the optical bonding described above, for example, ultraviolet light from an excimer lamp is used.

The second flow path device 1 and the connection member 2 each have an outer shape of a rectangular plate as viewed in plan, similarly to, for example, the first flow path device 3. For example, the second upper surface 1a, the second lower surface 1b, the third upper surface 2a, and the third lower surface 2b are perpendicular to the positive Z-direction, similarly to the first upper surface 3a and the first lower surface 3b.

Figure 19:
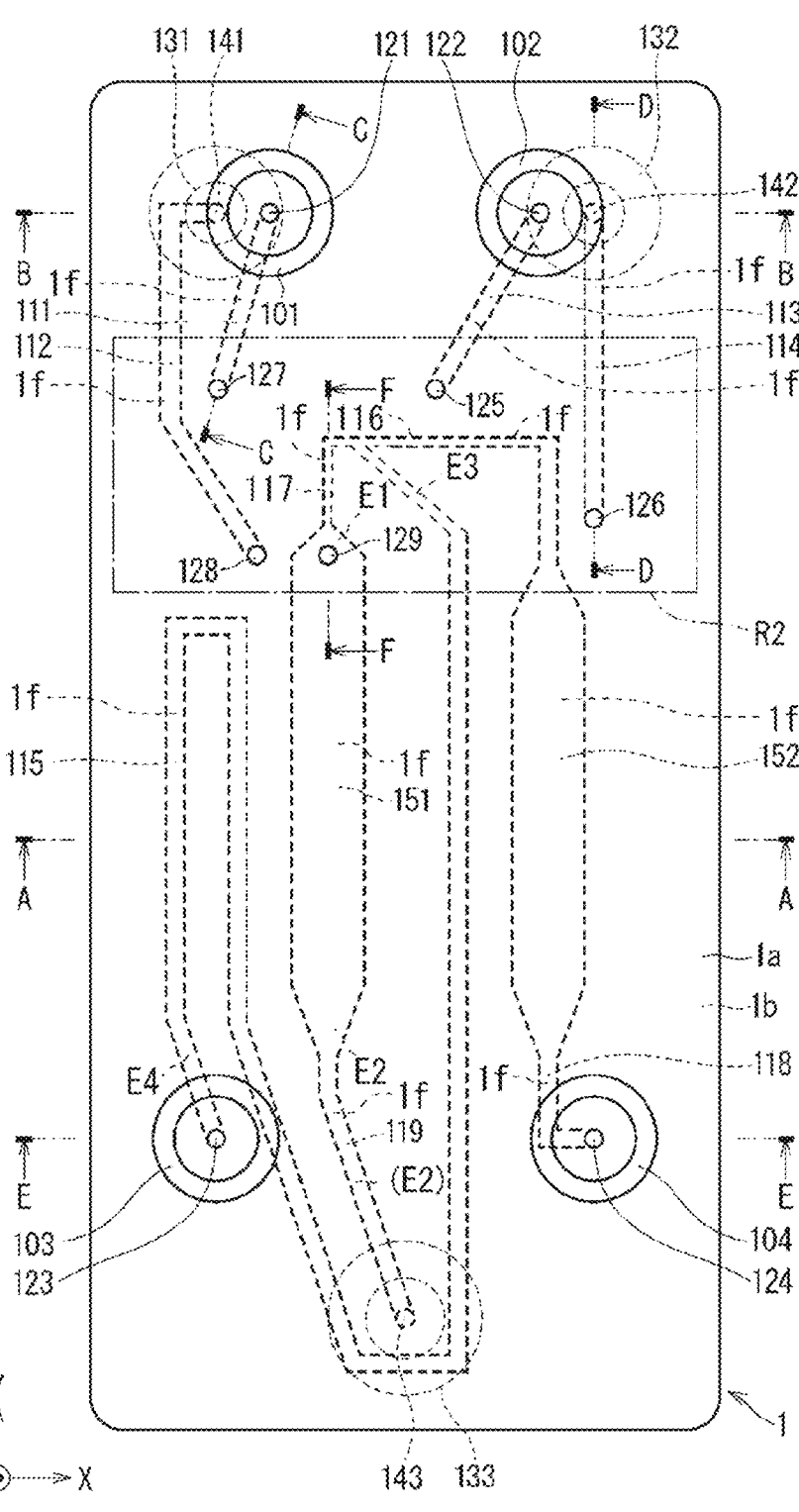
FIG. 19 is a schematic plan view of an example second flow path device.
Figure 20:
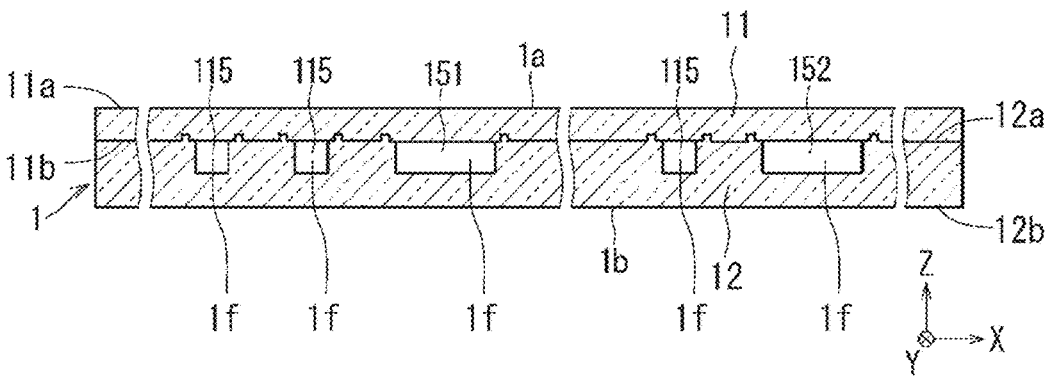
FIG. 20 is a schematic imaginary example cross-sectional view of the separating processing device at position A-A as viewed in a positive Y-direction.
Figure 21:
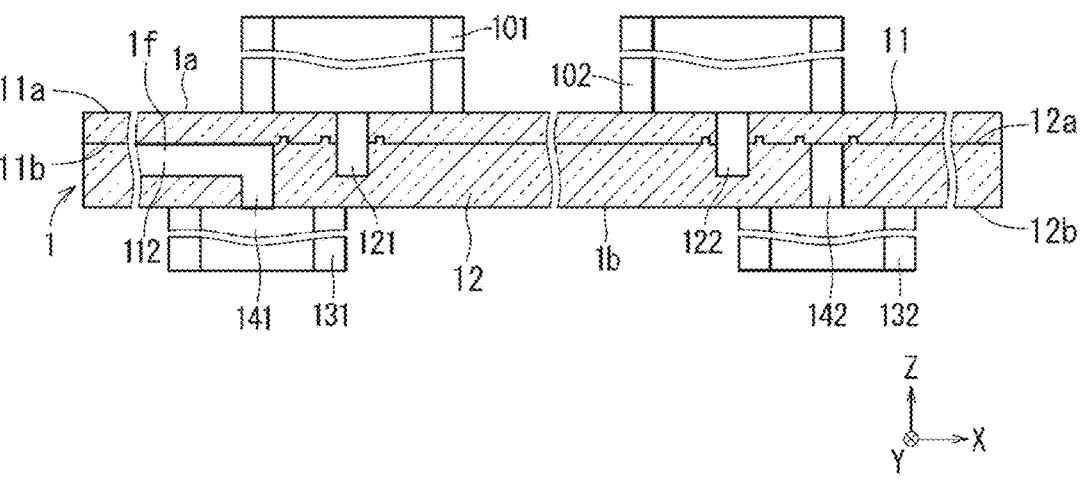
FIG. 21 is a schematic imaginary example cross-sectional view of the separating processing device at position B-B as viewed in the positive Y-direction.
Figure 22:
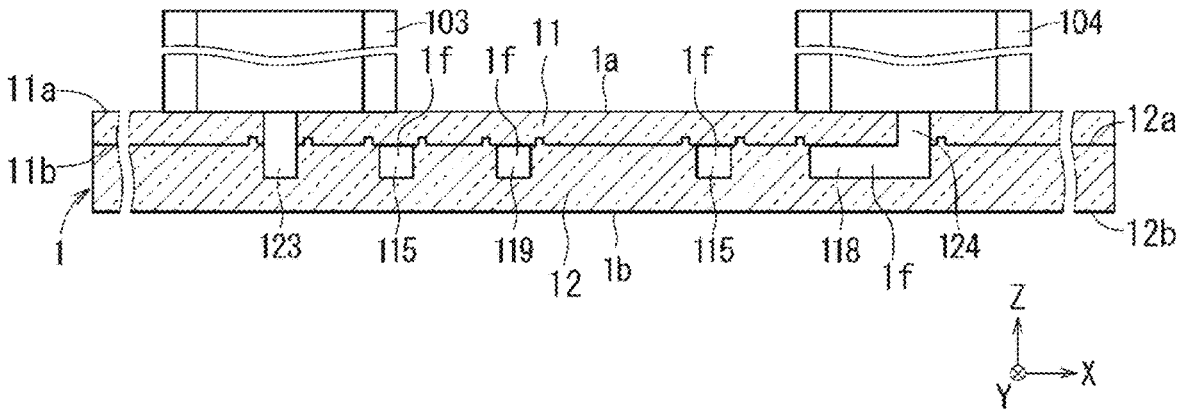
FIG. 22 is a schematic imaginary example cross-sectional view of the separating processing device at position E-E as viewed in the positive Y-direction.
Figure 23:
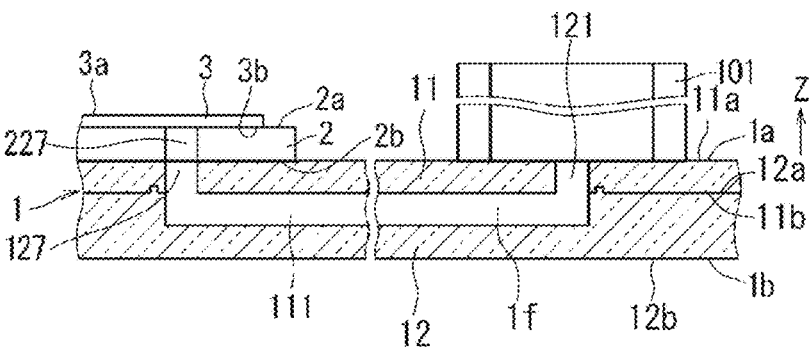
FIG. 23 is a schematic imaginary example cross-sectional view of the separating processing device at position C-C as viewed in a direction perpendicular to a positive Z-direction.
Figure 24:
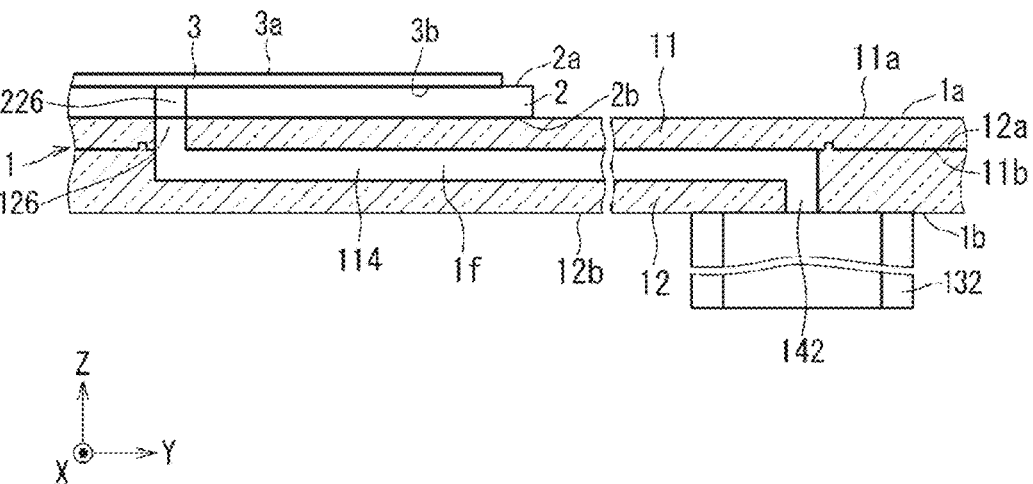
FIG. 24 is a schematic imaginary example cross-sectional view of the separating processing device at position D-D as viewed in a negative X-direction.
Figure 25:
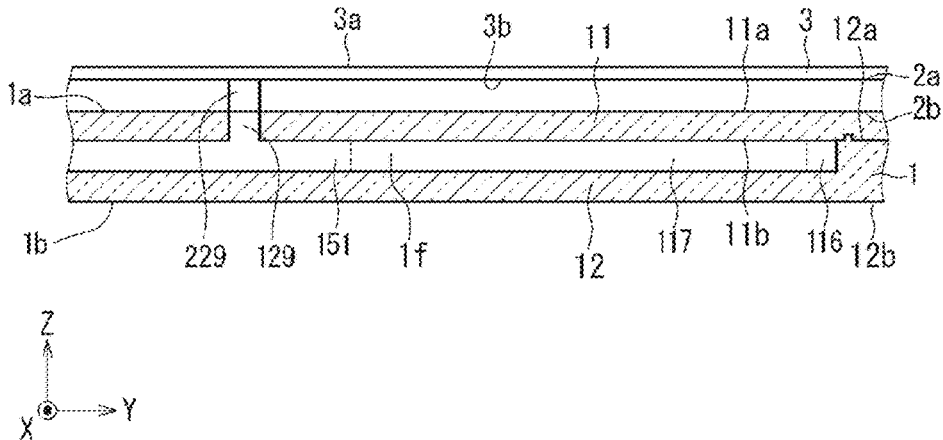
FIG. 25 is a schematic imaginary example cross-sectional view of the separating processing device at position F-F as viewed in the negative X-direction.

FIG. 19 is a schematic plan view of an example of the second flow path device 1. In FIG. 19, a rectangular area R2 defined by a dot-dash line is an area in which the third lower surface 2b of the connection member 2 is bonded on the second upper surface 1a. In the second flow path device 1, for example, an area of the second upper surface 1a other than the area R2, the second lower surface 1b, and side surfaces connecting the second upper surface 1a and the second lower surface 1b serve as an outer surface of the separating processing device 100.

The second flow path device 1 has a thickness of, for example, about 0.5 to 5 mm. The thickness of the second flow path device 1 refers to the dimension of the second flow path device 1 in the positive Z-direction. The second upper surface 1a and the second lower surface 1b each have a width of, for example, about 10 to 50 mm. The width of the second upper surface 1a refers to the dimension of the second upper surface 1a in the positive X-direction. The width of the second lower surface 1b refers to the dimension of the second lower surface 1b in the positive X-direction. The second upper surface 1a and the second lower surface 1b each have a length of, for example, about 20 to 100 mm. The length of the second upper surface 1a refers to the dimension of the second upper surface 1a in the positive Y-direction. The length of the second lower surface 1b refers to the dimension of the second lower surface 1b in the positive Y-direction.

The second flow path device 1 includes, for example, six inlet holes 121, 122, 124, 126, 128, and 129, two outlet holes 125 and 127, and a stirring hole 123. The three inlet holes 126, 128, and 129 and the two outlet holes 125 and 127 are each open in the second upper surface 1a in the area R2. The three inlet holes 121, 122, and 124 and the stirring hole 123 are each open in the second upper surface 1a outside the area R2. The six inlet holes 121, 122, 124, 126, 128, and 129, the two outlet holes 125 and 127, and the stirring hole 123 each have an opening that is open in the second upper surface 1a. In other words, any of the six inlet holes 121, 122, 124, 126, 128, and 129, the two outlet holes 125 and 127, and the stirring hole 123 is not open in the second lower surface 1b.

The second flow path device 1 includes, for example, three outlet holes 141, 142, and 143. The three outlet holes 141, 142, and 143 are each open in the second lower surface 1b outside the area R2. The three outlet holes 141, 142, and 143 each have an opening that is open in the second lower surface 1b. In other words, any of the outlet holes 141, 142, and 143 is not open in the second upper surface 1a.

The second flow path device 1 includes, for example, multiple flow paths 1f. The multiple flow paths 1f include, for example, a stirring flow path 115, eight flow paths 111, 112, 113, 114, 116, 117, 118, and 119, a measurement flow path 151, and a reference flow path 152. The multiple flow paths 1f are each a groove that is not open in either the second upper surface 1a or the second lower surface 1b.

The flow path 111 is continuous with the inlet hole 121 and the outlet hole 127. The flow path 112 is continuous with the inlet hole 128 and the outlet hole 141. The flow path 113 is continuous with the inlet hole 122 and the outlet hole 125. The flow path 114 is continuous with the inlet hole 126 and the outlet hole 142.

The measurement flow path 151 is between the flow path 117 and the flow path 119. The measurement flow path 151 has a direction (also referred to as a first longitudinal direction) in which the measurement flow path 151 extends. In the example in FIG. 19, the first longitudinal direction is parallel to the negative Y-direction from the flow path 117 toward the flow path 119. In other words, the measurement flow path 151 extends in the negative Y-direction. The measurement flow path 151 has an end in the positive Y-direction connected to the flow path 117 and an end in the direction opposite to the positive Y-direction (in the negative Y-direction) connected to the flow path 119. The measurement flow path 151 is connected to the flow path 117 at a position overlapping the area R2 as viewed in plan.

The measurement flow path 151 includes an area (also referred to as a first end area) E1 located at one end in the first longitudinal direction and an area (also referred to as a second end area) E2 at the other end opposite to the first end area E1 in the first longitudinal direction. In other words, the measurement flow path 151 includes the first end area E1 and the second end area E2 opposite to each other in the first longitudinal direction. In the example in FIG. 19, the first end area E1 is located at the end of the measurement flow path 151 in the positive Y-direction, and the second end area E2 is located at the end of the measurement flow path 151 in the negative Y-direction. The inlet hole 129 is connected to the first end area E1 in the measurement flow path 151. Thus, the inlet hole 129 is connected to the measurement flow path 151 and open in the second upper surface 1a.

The measurement flow path 151 is connected to the flow path 117 in the first end area E1. In the example in FIG. 19, the measurement flow path 151 includes the first end area E1 continuous with the stirring flow path 115 through the flow path 117 and a part of the flow path 116. "A first portion being continuous with a second portion" refers to the first portion being directly continuous with the second portion to allow a fluid to flow between the first portion and the second portion or refers to the first portion being continuous with the second portion through another portion (a third portion) to allow a fluid to flow between the first portion and the second portion. Thus, the measurement flow path 151 includes the first end area E1 continuous with the stirring flow path 115.

The flow path 116 is between the flow path 117 and the reference flow path 152 and is connected to the stirring flow path 115 between the flow path 117 and the reference flow path 152. The flow path 117 is between the measurement flow path 151 and the flow path 116. The flow path 118 is connected to the inlet hole 124 and is between the inlet hole 124 and the reference flow path 152. The flow path 119 is between the outlet hole 143 and the measurement flow path 151 and is connected to the outlet hole 143. Thus, the outlet hole 143 is continuous with the measurement flow path 151 through the flow path 119 and is open in the second lower surface 1b. More specifically, the outlet hole 143 is continuous with the second end area E2 in the measurement flow path 151 through the flow path 119.

The stirring flow path 115 is between the stirring hole 123 and the flow path 116. The stirring flow path 115 has a direction (also referred to as a second longitudinal direction) in which the stirring flow path 115 extends. The stirring flow path 115 bends in the example in FIG. 19. More specifically, the stirring flow path 115 extends in different directions from the stirring hole 123 to the flow path 116, extending in the positive Y-direction, in the positive X-direction, in the negative Y-direction, in the positive X-direction, and then in the positive Y-direction.

The stirring flow path 115 includes an area (also referred to as a third end area) E3 at one end in the second longitudinal direction and an area (also referred to as a fourth end area) E4 at the other end opposite to the third end area E3 in the second longitudinal direction. In other words, the stirring flow path 115 includes the third end area E3 and the fourth end area E4 opposite to each other in the second longitudinal direction. The stirring flow path 115 is continuous with the measurement flow path 151 in the third end area E3 through a part of the flow path 116 and the flow path 117. The stirring flow path 115 is connected to the stirring hole

123 in the fourth end area E4. Thus, the stirring hole 123 is continuous with the fourth end area E4 in the stirring flow path 115 and is open in the second upper surface 1*a*.

The reference flow path 152 is between the flow path 116 and the flow path 118. The reference flow path 152 extends in the positive Y-direction. The reference flow path 152 has an end in the positive Y-direction connected to the flow path 116 and an end in the direction opposite to the positive Y-direction (in the negative Y-direction) connected to the flow path 118. In the example in FIG. 19, the measurement flow path 151 and the reference flow path 152 both extend in the positive Y-direction. However, the measurement flow path 151 and the reference flow path 152 may extend in different directions.

FIGS. 20 to 25 are imaginary cross-sectional views of the separating processing device 100.

The second flow path device 1 includes, for example, a first plate 11 and a second plate 12 stacked on each other. In other words, in the examples in FIGS. 20 to 25, the first plate 11 and the second plate 12 are stacked on each other in the stated order in the negative Z-direction. The first plate 11 includes a first surface 11*a* and a second surface 11*b* opposite to the first surface 11*a*. The first surface 11*a* is located in the positive Z-direction from the second surface 11*b*. The second plate 12 includes a third surface 12*a* and a fourth surface 12*b* opposite to the third surface 12*a*. The third surface 12*a* is located in the positive Z-direction from the fourth surface 12*b*.

The first plate 11 and the second plate 12 are bonded together with the third surface 12*a* partially bonded to the second surface 11*b*. The first plate 11 and the second plate 12 thus form the second flow path device 1 being integral. The first plate 11 and the second plate 12 may be bonded with, for example, any welding method such as ultrasonic welding, laser welding, heat welding, or diffusion welding. In the second flow path device 1, the first surface 11*a* corresponds to the second upper surface 1*a*, and the fourth surface 12*b* corresponds to the second lower surface 1*b*. The multiple flow paths 1*f* are each defined between the second surface 11*b* and the third surface 12*a*. More specifically, the stirring flow path 115, the eight flow paths 111, 112, 113, 114, 116, 117, 118, and 119, the measurement flow path 151, and the reference flow path 152 are each defined between the second surface 11*b* and the third surface 12*a*. The six inlet holes 121, 122, 124, 126, 128, and 129, the two outlet holes 125 and 127, and the stirring hole 123 each extend through the first plate 11. The three outlet holes 141, 142, and 143 each extend through the second plate 12.

The stirring flow path 115 extends from the stirring hole 123 substantially in the positive Y-direction, in the positive X-direction by a short distance, substantially in the negative Y-direction, in the positive X-direction by a short distance, substantially in the positive Y-direction, and then to the flow path 116 and is connected to the flow path 116. The portion of the stirring flow path 115 connected to the flow path 116 inclines in the negative X-direction with respect to the positive Y-direction as the stirring flow path 115 extends in the positive Y-direction. The portion in the flow path 116 connected to the stirring flow path 115 extends in the negative X-direction. The flow path 116 and the stirring flow path 115 define a minor angle (also referred to as a first minor angle) at a position nearer the flow path 117. The flow path 116 and the stirring flow path 115 also define a minor angle (also referred to as a second minor angle) at a position opposite to the flow path 117. The first minor angle is greater than the second minor angle. This structure allows a liquid forced out of the stirring flow path 115 to the flow path 116 to easily move toward the measurement flow path 151 through the flow path 117. A flow path with less bending allows easier flow of a liquid.

The second flow path device 1 includes four cylinders 101, 102, 103, and 104 protruding from the second upper surface 1*a* in the positive Z-direction. The cylinder 101 surrounds the inlet hole 121 about the Z-axis as viewed in plan. The cylinder 102 surrounds the inlet hole 122 about the Z-axis as viewed in plan. The cylinder 103 surrounds the stirring hole 123 about Z-axis as viewed in plan. The cylinder 104 surrounds the inlet hole 124 about the Z-axis as viewed in plan.

The second flow path device 1 includes three cylinders 131, 132, and 133 protruding from the second lower surface 1*b* in the direction (negative Z-direction) opposite to the positive Z-direction. The cylinder 131 surrounds the outlet hole 141 about the Z-axis as viewed in plan. The cylinder 132 surrounds the outlet hole 142 about the Z-axis as viewed in plan. The cylinder 133 surrounds the outlet hole 143 about the Z-axis as viewed in plan.

Figure 26:
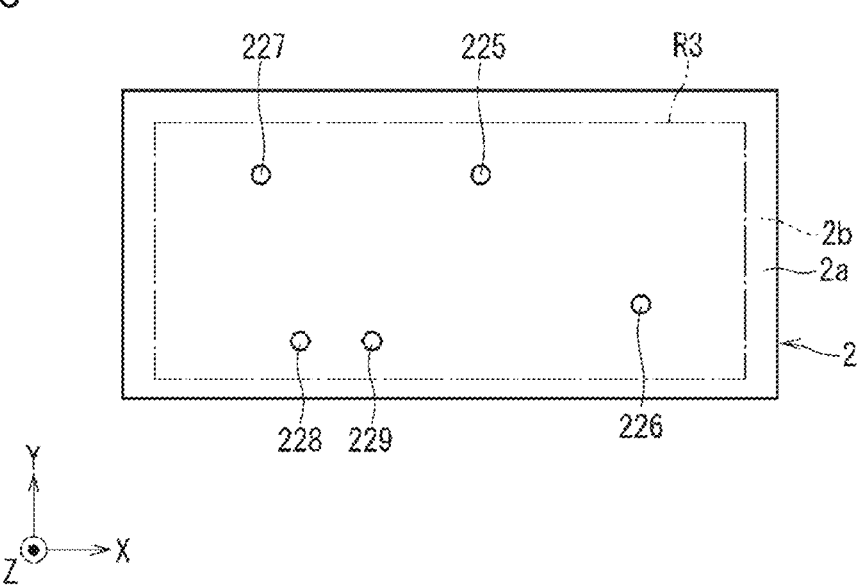
FIG. 26 is a schematic plan view of an example connection member.

FIG. 26 is a plan view of an example of the connection member 2. In FIG. 26, a rectangular area R3 defined by a dot-dash line is an area in which the first lower surface 3*b* is bonded.

The connection member 2 includes five through-holes 225, 226, 227, 228, and 229. The five through-holes 225, 226, 227, 228, and 229 each extend through from the third upper surface 2*a* to the third lower surface 2*b* in the area R3. The connection member 2 is, for example, in the form of a sheet.

The through-hole 227 is connected to the outlet hole 127 and to the inlet hole 327. In other words, the through-hole 227 connects the outlet hole 127 and the inlet hole 327. Thus, the inlet hole 327 is continuous with the inlet hole 121 through the through-hole 227, the outlet hole 127, and the flow path 111 in the stated order.

The through-hole 225 is connected to the outlet hole 125 and to the inlet hole 325. In other words, the through-hole 225 connects the outlet hole 125 and the inlet hole 325. Thus, the inlet hole 325 is continuous with the inlet hole 122 through the through-hole 225, the outlet hole 125, and the flow path 113 in the stated order.

The through-hole 226 is connected to the inlet hole 126 and to the outlet hole 326. In other words, the through-hole 226 connects the outlet hole 326 and the inlet hole 126. Thus, the outlet hole 326 is continuous with the outlet hole 142 through the through-hole 226, the inlet hole 126, and the flow path 114 in the stated order.

The through-hole 229 is connected to the inlet hole 129 and to the outlet hole 329. In other words, the through-hole 229 connects the outlet hole 329 and the inlet hole 129. Thus, the outlet hole 329 is continuous with the measurement flow path 151 through the through-hole 229 and the inlet hole 129 in the stated order.

The through-hole 228 is connected to the inlet hole 128 and to the outlet hole 328. In other words, the through-hole 228 connects the outlet hole 328 and the inlet hole 128. Thus, the outlet hole 328 is continuous with the outlet hole 141 through the through-hole 228, the inlet hole 128, and the flow path 112 in the stated order.

Overall Example Functions of Separating Processing Device

The functions of the separating processing device 100 are roughly described below.

As described above, the first liquid L1 as a process target containing the particles P100 and P200 of multiple types is introduced into the first flow path device 3. The first flow path device 3 separates the separating target particles P100 from the non-target particles P200 and discharges the separating target particles P100.

The second flow path device 1 is used to perform, for example, a predetermined process on the separating target particles P100. The predetermined process is, for example, to count the number of separating target particles P100 (count detection). To describe the processing, the separating target particles P100 and the liquid containing the separating target particles P100 are each hereafter also referred to as "a sample". The liquid containing the separating target particles P100 as the particles of the specific type is hereafter also referred to as "a particle-containing liquid".

The connection member 2 guides the separating target particles P100 (more specifically, the sample) discharged from the first flow path device 3 to the second flow path device 1.

In the first variation, for example, the second liquid L2 that functions as a pretreatment liquid is introduced through the inlet hole 121 as preparation before the first liquid L1 is introduced into the separating processing device 100. The second liquid L2 may facilitate cleaning of the separating processing device 100 and smooth movement of the first liquid L1 and the sample in the first flow path device 3. For example, when the first liquid L1 is introduced into the separating processing device 100, the second liquid L2 that functions as a flow-directing liquid is introduced into the separating processing device 100 through the inlet hole 121. The second liquid L2 introduced into the separating processing device 100 through the inlet hole 121 flows through the flow path 111, the outlet hole 127, the through-hole 227, the inlet hole 327, and the flow path 37 in the stated order, and then flows into the main flow path 34.

When the second liquid L2 is introduced into the separating processing device 100 through the inlet hole 121, for example, the liquid feeder 4 is connected to the inlet hole 121 to feed the second liquid L2 from the inlet hole 327 through the flow path 37 to the main flow path 34. More specifically, the liquid feeder 4 may be connected to the first inlet opening 1i of the inlet hole 327 through the inlet hole 121, the flow path 111, the outlet hole 127, and the through-hole 227.

Thus, in the first variation, the liquid feeder 4 is connected to the first inlet opening 1i of the inlet hole 327 to allow a liquid flow between the liquid feeder 4 and the first inlet opening 1i, with the liquid feeder 4 connected to the inlet hole 121 to allow a liquid flow between the liquid feeder 4 and the inlet hole 121. The liquid feeder 4 can thus be indirectly connected to the first inlet opening 1i of the inlet hole 327 to allow a liquid flow between the liquid feeder 4 and the first inlet opening 1i. With this structure, in the preparation process in each of the above embodiments, the liquid feeder 4 is connected to the inlet hole 121 to allow a liquid flow between the liquid feeder 4 and the inlet hole 121. For example, a tubular member to connect the liquid feeder 4 to the inlet hole 121 may be externally connected to the separating processing device 100. The tubular member connecting the liquid feeder 4 to the inlet hole 121 herein refers to the tubular member allowing a liquid flow between the liquid feeder 4 and the inlet hole 121. The tubular member may be connected using, for example, the cylinder 101. In this case, the third connection flow path 4c includes, for example, the tubular member for connecting the liquid feeder 4 to the inlet hole 121, and includes the inlet hole 121, the flow path 111, the outlet hole 127, and the through-hole 227.

When the first liquid L1 is introduced into the separating processing device 100 through the inlet hole 122, for example, the suction-discharge unit 7 may be connected to the inlet hole 122 with the switcher 5 between the suction-discharge unit 7 and the inlet hole 122 to feed the first liquid L1 through the inlet hole 325 and the flow path 35 to the main flow path 34. More specifically, the first port 51 in the switcher 5 may be connected to the second inlet opening 2i of the inlet hole 325 through the inlet hole 122, the flow path 113, the outlet hole 125, and the through-hole 225.

Thus, in the first variation, the first port 51 in the switcher 5 is connected to the second inlet opening 2i of the inlet hole 325 to allow a liquid flow between the first port 51 and the second inlet opening 2i, with the first port 51 connected to the inlet hole 122 to allow a liquid flow between the first port 51 and the inlet hole 122. The first port 51 in the switcher 5 can thus be indirectly connected to the second inlet opening 2i of the inlet hole 325 to allow a liquid flow between the first port 51 and the second inlet opening 2i. With this structure, in the preparation process in each of the above embodiments, the first port 51 in the switcher 5 is connected to the inlet hole 122 to allow a liquid flow between the first port 51 and the inlet hole 122. For example, a tubular member to connect the first port 51 in the switcher 5 to the inlet hole 122 may be externally connected to the separating processing device 100. The tubular member connecting the first port 51 to the inlet hole 122 herein refers to the tubular member allowing a liquid flow between the first port 51 and the inlet hole 122. The tubular member may be connected using, for example, the cylinder 102. In this case, the first connection flow path 5c includes, for example, the tubular member for connecting the first port 51 in the switcher 5 to the inlet hole 122, and includes the inlet hole 122, the flow path 113, the outlet hole 125, and the through-hole 225.

In the first variation, for example, the first liquid L1 is introduced into the separating processing device 100 through the inlet hole 122. The first liquid L1 introduced into the separating processing device 100 through the inlet hole 122 flows through the flow path 113, the outlet hole 125, the through-hole 225, the inlet hole 325, and the flow path 35 in the stated order, and then flows into the main flow path 34.

In the first variation with this structure, as in each of the above embodiments, for example, the preparation process may be performed as illustrated in FIG. 6 to establish a connection between the first flow path device 3 and the switcher 5 to allow a liquid flow between the first flow path device 3 and the switcher 5, establish a connection between the switcher 5 and the internal space of the liquid storage 6 to allow a liquid flow between the switcher 5 and the internal space, establish a connection between the suction-discharge unit 7 and the switcher 5 to allow a liquid flow between the suction-discharge unit 7 and the switcher 5, and establish a connection between the liquid feeder 4 and the first flow path device 3 to allow a liquid flow between the liquid feeder 4 and the first flow path device 3. In this preparation process, a connection is established between the first flow path device 3 and the switcher 5 to allow a liquid flow between the second inlet opening 2i in the first flow path device 3 and the first port 51 in the switcher 5. In this preparation process, a connection is established between the second port 52 in the switcher 5 and the internal space of the liquid storage 6 to allow a liquid flow between the second port 52 and the internal space. In this preparation process, a connection is established between the third port 53 in the switcher 5 and the suction-discharge unit 7 to allow a liquid flow between the third port 53 and the suction-discharge unit 7. In this preparation process, a connection is established between the liquid feeder 4 and the first inlet opening 1*i* in the first flow path device 3 to allow a liquid flow between the liquid feeder 4 and the first inlet opening 1*i*.

In the first variation, as in the first embodiment, for example, the filling process illustrated in FIG. 7, the first suction process illustrated in FIG. 8, the pressurizing process illustrated in FIG. 9, and the introduction process illustrated in FIG. 10 may be performed. In the first variation, as in the second embodiment, for example, the filling process illustrated in FIG. 7, the first suction process illustrated in FIG. 8, the mixing process illustrated in FIG. 12, the pressurizing process illustrated in FIG. 13, and the introduction process illustrated in FIG. 14 may be performed. In the first variation, as in the third embodiment, for example, the filling process illustrated in FIG. 7, the second suction process illustrated in FIG. 16, the first suction process illustrated in FIG. 17, the pressurizing process illustrated in FIG. 13, and the introduction process illustrated in FIG. 14 may be performed.

In the filling process in the first variation, the liquid feeder 4 feeds the second liquid L2 to fill, with the second liquid L2, the flow path from the liquid feeder 4 through the inlet hole 121, the flow path 111, the outlet hole 127, the through-hole 227, the first inlet opening 1*i*, the flow path portion 30, the second inlet opening 2*i*, the through-hole 225, the outlet hole 125, the flow path 113, the inlet hole 122, the first port 51, and the second port 52 to the liquid storage 6. In the introduction process in the first variation, the suction-discharge unit 7 introduces the first liquid L1 or the liquid mixture L1*a* into the flow path portion 30 through the third port 53, the first port 51, the inlet hole 122, the flow path 113, the outlet hole 125, the through-hole 225, and the second inlet opening 2*i*. In each of the mixing process and the second suction process in the first variation, the suction-discharge unit 7 sucks the second liquid L2 from the flow path portion 30 through the second inlet opening 2*i*, the through-hole 225, the outlet hole 125, the flow path 113, the inlet hole 122, the first port 51, and the third port 53 into the suction-discharge unit 7.

In the first variation, for example, the second liquid L2 may be introduced from the flow path 37 through the main flow path 34 and the flow path 38 to the outlet hole 328, and then through the through-hole 228, the inlet hole 128, and the flow path 112 in this order to the outlet hole 141 during the period after the start of the filling process before the start of the introduction process. For example, the second liquid L2 may be introduced from the flow path 37 through the main flow path 34, the branch flow paths 31, and the flow path 36 in this order to the outlet hole 326, and then through the through-hole 226, the inlet hole 126, and the flow path 114 in this order to the outlet hole 142 during the period after the start of the filling process before the start of the introduction process. For example, the second liquid L2 flows from the flow path 37 through the main flow path 34 and the flow path 39 to the outlet hole 329, and then flows through the through-hole 229 and the inlet hole 129 and reaches the measurement flow path 151 during the period after the start of the filling process before the start of the introduction process. The second liquid L2 reaching the measurement flow path 151 may further be introduced through the flow path 119 into the outlet hole 143.

For example, a fluid for stirring (also referred to as a stirring fluid) is fed into the separating processing device 100 through the stirring hole 123. For example, the stirring fluid is discharged from the separating processing device 100 through the stirring hole 123. For example, a tubular member may be externally connected to the separating processing device 100 to feed and discharge the stirring fluid into and from the separating processing device 100 through the stirring hole 123 using the cylinder 103.

For example, a liquid for dispersion (also referred to as a dispersing liquid) is introduced into the separating processing device 100 through the inlet hole 124. For example, a tubular member may be externally connected to the separating processing device 100 to introduce the dispersing liquid into the separating processing device 100 through the inlet hole 124 using the cylinder 104.

As described above, the first flow path device 3 separates, among the particles of multiple types in the first liquid L1, the separating target particles P100 from the non-target particles P200 and discharges the separating target particles P100.

The non-target particles P200 to be discharged through the outlet hole 326 in the first flow path device 3 flow through the through-hole 226, the inlet hole 126, and the flow path 114 in the stated order, and then are discharged through the outlet hole 142 in the second flow path device 1. The non-target particles P200 discharged through the outlet hole 142 may or may not undergo a specific process.

The separating target particles P100 to be discharged through the outlet hole 329 in the first flow path device 3 flow through the through-hole 229 and the inlet hole 129 in the stated order, and then are introduced into the measurement flow path 151 in the second flow path device 1. The inlet hole 129 is open in the second upper surface 1*a*. Thus, when the separating processing device 100 is used with the second upper surface 1*a* facing upward and the second lower surface 1*b* facing downward, the sample may be easily introduced into the measurement flow path 151 from above through the inlet hole 129.

In the first variation, the first flow path device 3 is located on the second upper surface 1*a* of the second flow path device 1. The outlet hole 329 being open in the first lower surface 3*b* of the first flow path device 3 is connected to the inlet hole 129 being open in the second upper surface 1*a* of the second flow path device 1. Thus, when the first liquid L1 is introduced into the flow path portion 30 in the first flow path device 3, for example, the liquid (also referred to as the sample) containing the separating target particles P100 separated from the first liquid L1 in the flow path portion 30 may be fed into the measurement flow path 151 in the second flow path device 1 through the outlet hole 329 and the inlet hole 129. This may allow, for example, separating of the sample from the first liquid L1 using the first flow path device 3 and the predetermined process on the separating target particles P100 using the second flow path device 1 to be performed efficiently.

The remaining component to be discharged through the outlet hole 328 in the first flow path device 3 flows through the through-hole 228, the inlet hole 128, and the flow path 112 in the stated order, and then is discharged through the outlet hole 141 in the second flow path device 1. The remaining component discharged through the outlet hole 141 may or may not undergo a specific process.

The dispersing liquid introduced into the separating processing device 100 through the inlet hole 124 flows through the flow path 118, the reference flow path 152, the flow path 116, and the flow path 117 in the stated order, and then flows into the measurement flow path 151. The dispersing liquid disperses the separating target particles P100 introduced into the measurement flow path 151 through the inlet hole 129. "Dispersing" herein is an antonym of clumping or aggregation of the separating target particles P100. Dispersing the separating target particles P100 may allow the predetermined process, such as counting as referred to in the first variation, to be performed easily or accurately, or both easily and accurately. The dispersing liquid may be the same liquid as the second liquid L2. For the first liquid L1 being blood, the dispersing liquid is, for example, PBS. The dispersing liquid may be a liquid of PBS containing at least one of EDTA as the second element or BSA as the third element.

The stirring fluid introduced into the separating processing device 100 through the stirring hole 123 flows into the stirring flow path 115. The stirring fluid flows back and forth in the stirring flow path 115 with an external operation. The stirring fluid is, for example, air. In this case, the air pressure at the stirring hole 123 is controlled to cause the stirring fluid to flow back and forth through the stirring flow path 115. The stirring fluid is a fluid for stirring the dispersing liquid containing the separating target particles P100 to facilitate dispersion of the sample in the dispersing liquid in an area from the stirring flow path 115 through the flow paths 116 and 117 to the measurement flow path 151. In other words, the stirring fluid is a fluid for stirring the liquid (particle-containing liquid) containing the separating target particles P100 as the particles of the specific type. The stirring fluid may be the same liquid as the second liquid L2. For the first liquid L1 being blood, the stirring fluid is, for example, PBS. In this case, PBS flows back and forth through the stirring flow path 115 as the PBS flows into and out of the stirring flow path 115 through the stirring hole 123. The stirring fluid flowing back and forth in the stirring flow path 115 facilitates stirring of the dispersing liquid and the sample in the stirring flow path 115, in the flow paths 116 and 117, and in at least a part of the measurement flow path 151.

For example, the sample containing the particles of the specific type is introduced through the inlet hole 129 into an area nearer the first end area E1 in the measurement flow path 151. The stirring fluid is repeatedly fed into and discharged from the stirring flow path 115 through the stirring hole 123, thus facilitating stirring of the dispersing liquid and the sample. The dispersing liquid being stirred with the sample may facilitate, for example, dispersion of the separating target particles P100. The stirring fluid may be a liquid of PBS containing at least one of EDTA as the second element or BSA as the third element.

The sample and the dispersing liquid move toward the flow path 119 in the measurement flow path 151. The stirring fluid, in addition to the sample and the dispersing liquid, may also move toward the flow path 119 in the measurement flow path 151. The measurement flow path 151 is used to perform the predetermined process on the separating target particles P100. The predetermined process may be, for example, counting the number of separating target particles P100 in the sample in a specific area in the measurement flow path 151 by optical measurement.

After the predetermined process is performed on the separating target particles P100 in the measurement flow path 151, the sample and the dispersing liquid flow from the measurement flow path 151 through the flow path 119 and are discharged through the outlet hole 143. The outlet hole 143 is open in the second lower surface 1b. Thus, when the second flow path device 1 is used with the second upper surface 1a facing upward and the second lower surface 1b facing downward, the sample may easily flow from the measurement flow path 151 through the flow path 119 and be discharged through the outlet hole 143. The stirring fluid, in addition to the sample and the dispersing liquid, may also flow from the measurement flow path 151 through the flow path 119 and be discharged through the outlet hole 143. The separating target particles P100 discharged through the outlet hole 143 may or may not undergo a specific process.

The material for the second flow path device 1 is, for example, a resin such as a cycloolefin polymer (COP). The second flow path device 1 made of a COP may be less flexible. In this case, the materials for the first plate 11 and the second plate 12 are both COPs. The first plate 11 and the second plate 12 may each be manufactured by, for example, resin molding. The material for the second flow path device 1 may be, for example, an acrylic resin or polycarbonate (PC). The acrylic resin is, for example, polymethyl methacrylate (PMMA).

3-2. Other Examples

In each of the above embodiments, for example, at least one hole selected from the two inlet holes 325 and 327 and the three outlet holes 326, 328, and 329 may not be open in the first lower surface 3b and may be open in the first upper surface 3a. In other words, for example, the two inlet holes 325 and 327 and the three outlet holes 326, 328, and 329 may each be open in the first upper surface 3a or the first lower surface 3b. In each of the above embodiments, the first flow path device 3 includes the single set of the inlet hole 325 and the flow path 35 as a unit for introducing the first liquid L1. However, the first flow path device 3 may include two or more sets of the inlet hole 325 and the flow path 35 as units for introducing the first liquid L1. In each of the above embodiments, the first flow path device 3 includes the single set of the inlet hole 327 and the flow path 37 as a unit for introducing the second liquid L2. However, the first flow path device 3 may include two or more sets of the inlet hole 327 and the flow path 37 as units for introducing the second liquid L2. In these cases, each of the units for introducing the liquids is to be appropriately connected to the main flow path 34 to allow the first flow path device 3 to function as a separating flow path device.

In each of the above embodiments, for example, when the second liquid L2 is introduced into the first flow path device 3 through the first inlet opening 1i, a liquid suction unit may be connected to the outlet hole 326 to suck the second liquid L2 from the main flow path 34 through the multiple branch flow paths 31 and the outlet hole 326. In this case, for example, a tubular member to connect the liquid suction unit to the outlet hole 326 may be externally connected to the first flow path device 3. The tubular member connecting the liquid suction unit to the outlet hole 326 herein refers to the tubular member allowing a liquid flow between the liquid suction unit and the outlet hole 326. To connect the tubular member, for example, the first lower surface 3b of the first flow path device 3 may include a cylindrical portion protruding in the negative Z-direction and surrounding the outlet hole 326 about the Z-axis as viewed in plan.

In the first variation, for example, when the second liquid L2 is introduced into the separating processing device 100 through the inlet hole 121, a liquid suction unit may be connected to the outlet hole 142 to suck the second liquid L2 from the main flow path 34 through the multiple branch flow paths 31 and the outlet hole 326. In this case, for example, a tubular member to connect the liquid suction unit to the outlet hole 142 may be externally connected to the separating processing device 100. The tubular member connecting the liquid suction unit to the outlet hole 142 herein refers to the tubular member allowing a liquid flow between the liquid suction unit and the outlet hole 142. The tubular member may be connected using, for example, the cylinder 132. The liquid suction unit can suck the second liquid L2 from, for example, the main flow path 34 through the multiple branch flow paths 31, the flow path 36, the outlet hole 326, the through-hole 226, the inlet hole 126, the flow path 114, and the outlet hole 142.

In the first variation, for example, the flow path portion 30 may be a groove that is not open in the first upper surface 3*a* and is open in the first lower surface 3*b*. In this case, the first lower surface 3*b* of the first flow path device 3 is in contact with the third upper surface 2*a* excluding portions with the two inlet holes 325 and 327, the three outlet holes 326, 328, and 329, and the flow path portion 30. A fluid does not move in a portion between the first lower surface 3*b* and the third upper surface 2*a* in contact with each other. The flow path portion 30 is used together with the third upper surface 2*a* to allow the fluid to move. The first flow path device 3 may include, for example, the connection member 2. In the structure with the connection member 2, for example, the flow path portion 30 is not open in the outer surface of the first flow path device 3 and is located inside the first flow path device 3. For example, the inlet hole 327 may include the through-hole 227. For example, the inlet hole 325 may include the through-hole 225. For example, the outlet hole 329 may include the through-hole 229. For example, the outlet hole 326 may include the through-hole 226. For example, the outlet hole 328 may include the through-hole 228. In this case, for example, the two inlet holes 325 and 327 and the three outlet holes 326, 328, and 329 are each continuous with the flow path portion 30 and are open in the outer surface of the first flow path device 3. In other words, for example, the first flow path device 3 includes, inside the first flow path device 3, the flow path portion 30 that allows a liquid flow between the first inlet opening 1*i* of the inlet hole 327 and the second inlet opening 2*i* of the inlet hole 325.

For example, the connection member 2 and the first flow path device 3 have a less flexible structure. For example, the first flow path device 3 made of PDMS and the connection member 2 made of a silicone resin are both flexible. The second flow path device 1 made of a COP is less flexible and is less likely to deteriorate the function of the first flow path device 3. The second flow path device 1 made of, for example, a material that is not easily bonded directly to the material for the first flow path device 3 may be bonded to the first flow path device 3 easily with the connection member 2.

In the first variation, for example, the second flow path device 1 may include at least the measurement flow path 151 of the multiple flow paths 1*f*. In this case, for example, the first flow path device 3 may not be stacked on the second flow path device 1, and the outlet hole 329 in the first flow path device 3 and the inlet hole 129 in the second flow path device 1 may be connected to each other through, for example, a tubular member. In the first flow path device 3, the first liquid L1 may be introduced into the inlet hole 325 through, for example, a tubular member, and the second liquid L2 may be introduced into the inlet hole 327 through, for example, a tubular member. In the first flow path device 3, the non-target particles P200 may be discharged through the outlet hole 326 through, for example, a tubular member, and the remaining component of the first liquid L1 other than the non-target particles P200 and the separating target particles P100 may be discharged through the outlet hole 328 through, for example, a tubular member.

In the first variation, for example, the measurement flow path 151 may not be continuous with the outlet hole 143 through the flow path 119 and may be directly connected to the outlet hole 143. In other words, the outlet hole 143 may be directly connected to the second end area E2 in the measurement flow path 151. In this structure as well, the outlet hole 143 is continuous with the second end area E2 in the measurement flow path 151.

In the first variation, for example, the first flow path device 3 may not be located on the second flow path device 1 with the connection member 2 between the first flow path device 3 and the second flow path device 1. In this case, for example, the first lower surface 3*b* of the first flow path device 3 may be in contact with the second upper surface 1*a* of the second flow path device 1. For example, the three inlet holes 126, 128, and 129 and the two outlet holes 125 and 127 in the second flow path device 1 may be connected to the three outlet holes 326, 328, and 329 and the two inlet holes 325 and 327 in the first flow path device 3 through, for example, tubular members. For example, the inlet hole 129 may be open in either the second upper surface 1*a* or the second lower surface 1*b*.

In the first variation, for example, the stirring hole 123 may not be open in the second upper surface 1*a* and may be open in the second lower surface 1*b*.

In the first variation, for example, when the separating target particles P100 undergo optical measurement as an example of the predetermined process, the separating processing device 100 may be an optical measurement device with an optical sensor unit as an additional component. In this case, the optical sensor unit may be, for example, a light sensor including a light emitter and a light receiver. The light emitter is, for example, a light-emitting element such as a light-emitting diode (LED) or a laser diode (LD). The light receiver is, for example, a light-receiving element such as a photodiode (PD). The light-receiving element is, for example, an element including a semiconductor substrate of a first conductivity type having a semiconductor region of a second conductivity type in a surface layer near an upper surface of the semiconductor substrate. The light-emitting element may be, for example, an element including the semiconductor substrate described above and multiple semiconductor layers stacked on the semiconductor substrate. In this structure, light emitted from the light emitter may transmit through the sample in the measurement flow path 151 and may be received by the light receiver. Light emitted from the light emitter may transmit through the dispersing liquid in the reference flow path 152 and may be received by the light receiver. The light emitter and the light receiver in the optical sensor unit may be elements integral with a single semiconductor substrate as described above, or the light emitter and the light receiver may be an integral element placed on a single substrate. The optical sensor unit including the light emitter and the light receiver integral with each other on a single substrate can downsize the optical sensor unit and shorten the focal length of the optical sensor unit, thus allowing accurate measurement of microscopic areas. The optical sensor unit may be held by, for example, an actuator in a movable manner between a position facing the measurement flow path 151 and a position facing the reference flow path 152. The optical measurement device may include a controller for controlling the operation of the optical sensor unit. The controller may control the operation of the actuator that moves the optical sensor unit. The controller may perform various computation processes based on a signal received from the light receiver that outputs the signal in response to receiving light. These functions of the controller may be included in the controller 9 described above.

In each of the above embodiments and the above examples, for example, the operation of the liquid feeder 4 may be performed manually, or the operation of the suction-discharge unit 7 may be performed manually. Although the suction-discharge unit 7 in each of the above examples is a syringe pump including the reservoir inside, the suction-discharge unit 7 may be, for example, an assembly including a reservoir as a container for storing a liquid and a suction-discharge device that performs the operation for sucking and discharging the liquid through the reservoir, with the reservoir and the suction-discharge device connected to each other with a tubular member. When the first liquid L1 is blood, for example, components contacted by the first liquid L1 are to be replaced before another blood sample is used as the first liquid L1. In the suction-discharge unit 7 including the reservoir and the suction-discharge device that are separate members connected to each other, the suction-discharge device can be used repeatedly by simply replacing the reservoir without replacing the entire suction-discharge unit 7.

In the first flow path device 3 in each of the above embodiments and the above examples, the flow path portion 30 may not include the flow path 38 as the seventh flow path, and the multiple holes 32 may not include the outlet hole 328 as the third outlet hole. In this case, for example, the flow path 39 as the fifth flow path may extend in the negative Y-direction as the first direction, similarly to the main flow path 34. The main flow path 34 may include, for example, the flow path 39 as the fifth flow path.

In each of the above embodiments and the above examples, the widths of the five flow paths 35, 36, 37, 38, and 39 may each not be constant in the upstream portion to the downstream portion. For example, the flow path 35 may include a portion with a width being narrower in a continuous or a stepwise manner from the inlet hole 325 to the main flow path 34. For example, the flow path 37 may include a portion with a width being narrower in a continuous or a stepwise manner from the inlet hole 327 to the main flow path 34. For example, the flow path 38 may include a portion with a width being wider in a continuous or a stepwise manner from the main flow path 34 to the outlet hole 328. For example, the flow path 39 may include a portion with a width being wider in a continuous or a stepwise manner from the main flow path 34 to the outlet hole 329.

In each of the above embodiments and the above examples, for example, the first liquid L1 may be a liquid containing multiple types of particles other than blood. In this case, the second liquid L2, the dispersing liquid, and the stirring fluid may each be, for example, any of various liquids corresponding to the first liquid L1. The various liquids may include, for example, water.

In each of the above embodiments and the above examples, the first flow path device 3 is not limited to a device with a structure to separate particles of a specific type in the first liquid L1. The first flow path device 3 may include, for example, the flow path portion inside the first flow path device 3 to allow a liquid flow between the first opening and the second opening, and may be designed to receive the first liquid L1 after the flow path portion is filled with the second liquid L2. Such a first flow path device 3 may have any structure other than the above-described structure for processing the first liquid L1. The first flow path device 3 with another structure may be, for example, a flow path device including a flow path portion 30 configured to mix multiple liquids, rather than to separate particles of a specific type in the first liquid L1.

The components described in the above embodiments and the variations may be entirely or partially combined as appropriate unless any contradiction arises.

The invention claimed is:

1. A method for introducing a liquid into a flow path device, the method comprising:

preparation including establishing a connection between a flow path device and a switcher to allow a liquid flow between a second opening in the flow path device and a first port in the switcher, the flow path device including a flow path portion inside the flow path device to allow a liquid flow between a first opening and the second opening in the flow path device, the switcher including the first port, a second port, and a third port and being selectively settable to one of a first state, a second state, or a third state, the preparation including establishing a connection between the second port and an internal space of a liquid storage to allow a liquid flow between the second port and the internal space, the liquid storage storing a first liquid, the preparation including establishing a connection between the third port and a suction-discharge unit to allow a liquid flow between the third port and the suction-discharge unit, the suction-discharge unit being configured to suck and discharge a liquid, the preparation including establishing a connection between the first opening and a liquid feeder to allow a liquid flow between the first opening and the liquid feeder, the liquid feeder being configured to feed a second liquid different from the first liquid, the first state being a state allowing a liquid flow between the first port and the second port, the second state being a state allowing a liquid flow between the second port and the third port, the third state being a state allowing a liquid flow between the first port and the third port;

filling after the preparation with the switcher being set to the first state, the filling including feeding the second liquid using the liquid feeder to fill, with the second liquid, a flow path from the liquid feeder through the first opening, the flow path portion, the second opening, the first port, and the second port to the liquid storage;

first suction after the filling with the switcher being set to the second state, the first suction including sucking the first liquid using the suction-discharge unit from the liquid storage through the second port and the third port into the suction-discharge unit; and introduction after the first suction with the switcher being set to the third state, the introduction including introducing the first liquid using the suction-discharge unit into the flow path portion through the third port, the first port, and the second opening.

2. The method according to claim 1, further comprising:

mixing between the first suction and the introduction with the switcher being set to the third state, the mixing including sucking the second liquid using the suction-discharge unit through the first port and the third port into the suction-discharge unit to mix the second liquid with the first liquid in the suction-discharge unit, wherein the introduction includes introducing, using the suction-discharge unit, the first liquid mixed with the second liquid in the mixing into the flow path portion through the third port, the first port, and the second opening.

3. The method according to claim 1, further comprising:

second suction between the filling and the first suction with the switcher being set to the third state, the second suction including sucking the second liquid using the suction-discharge unit through the first port and the third port into the suction-discharge unit, wherein the first suction includes sucking the first liquid using the suction-discharge unit from the liquid storage through the second port and the third port into the suction-discharge unit to mix the first liquid with the second liquid in the suction-discharge unit, and the introduction includes introducing, using the suction-discharge unit, the first liquid mixed with the second liquid in the first suction into the flow path portion through the third port, the first port, and the second opening.

4. The method according to claim 1, wherein
the first liquid is blood,
the second liquid is saline, and
the flow path device is a separating flow path device including, in the flow path portion, a main flow path and a branch flow path to separate particles in the blood.

5. The method according to claim 2, wherein the first liquid is blood, the second liquid is saline, and the flow path device is a separating flow path device including, in the flow path portion, a main flow path and a branch flow path to separate particles in the blood.

6. The method according to claim 3, wherein the first liquid is blood, the second liquid is saline, and the flow path device is a separating flow path device including, in the flow path portion, a main flow path and a branch flow path to separate particles in the blood.

* * * * *